United States Patent
Bright et al.

(10) Patent No.: US 11,267,882 B2
(45) Date of Patent: Mar. 8, 2022

(54) METHODS OF DETECTING HUMAN IL-21

(71) Applicant: Eli Lilly and Company, Indianapolis, IN (US)

(72) Inventors: Stuart Willis Bright, Carmel, IN (US); Julian Davies, La Jolla, CA (US); Andrea Paula Martin, Carmel, IN (US); Joshua Dade Poorbaugh, New Palestine, IN (US); Oliver Schroeder, San Diego, CA (US); Karen Leigh Cox, Martinsville, IN (US); Angus John MacDonald, Indianapolis, IN (US); Xiao-Fen Wang, San Diego, CA (US); Sean Edward Sissons, Bargersville, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 138 days.

(21) Appl. No.: 16/089,640

(22) PCT Filed: Mar. 24, 2017

(86) PCT No.: PCT/US2017/023946
§ 371 (c)(1),
(2) Date: Sep. 28, 2018

(87) PCT Pub. No.: WO2017/172509
PCT Pub. Date: Oct. 5, 2017

(65) Prior Publication Data
US 2019/0233508 A1    Aug. 1, 2019

Related U.S. Application Data

(60) Provisional application No. 62/316,127, filed on Mar. 31, 2016.

(51) Int. Cl.
*G01N 33/53* (2006.01)
*C07K 16/24* (2006.01)
*A61P 37/06* (2006.01)
*G01N 33/68* (2006.01)

(52) U.S. Cl.
CPC ............ *C07K 16/244* (2013.01); *A61P 37/06* (2018.01); *G01N 33/6869* (2013.01); *C07K 2317/51* (2013.01); *C07K 2317/515* (2013.01); *C07K 2317/92* (2013.01); *G01N 2333/54* (2013.01); *G01N 2800/101* (2013.01); *G01N 2800/104* (2013.01)

(58) Field of Classification Search
CPC .............. C07K 16/244; C07K 2317/51; C07K 2317/515; G01N 2333/54
See application file for complete search history.

(56) References Cited

U.S. PATENT DOCUMENTS

| | | | |
|---|---|---|---|
| 6,114,507 | A | 9/2000 | Shirakawa et al. |
| 2005/0266004 | A1 | 12/2005 | Giles-Komar et al. |
| 2012/0177655 | A1 | 7/2012 | Jaspers et al. |
| 2015/0266954 | A1 | 9/2015 | Davies et al. |

FOREIGN PATENT DOCUMENTS

WO    2015/142637 A1    9/2015

OTHER PUBLICATIONS

Weir et al. Cytokine 60 (2012) 220-225.

*Primary Examiner* — Dong Jiang
(74) *Attorney, Agent, or Firm* — Quarles & Brady LLP

(57) ABSTRACT

Provided are antibodies, or an antigen-binding fragment thereof, that binds human IL-21, These antibodies are useful in immunoassays of IL-21 levels, and/or in vivo, ex vivo or in vitro immunochemical and other imaging methods for determining the presence of IL-21 and/or quantifying IL-21 levels, and for diagnostic, prognostic and predictive purpose, and or optimizing therapeutic regimens in patients in which IL-21 signaling is implicated in pathogenesis.

10 Claims, 1 Drawing Sheet
Specification includes a Sequence Listing.

Individual data points for the healthy controls and diseased samples.
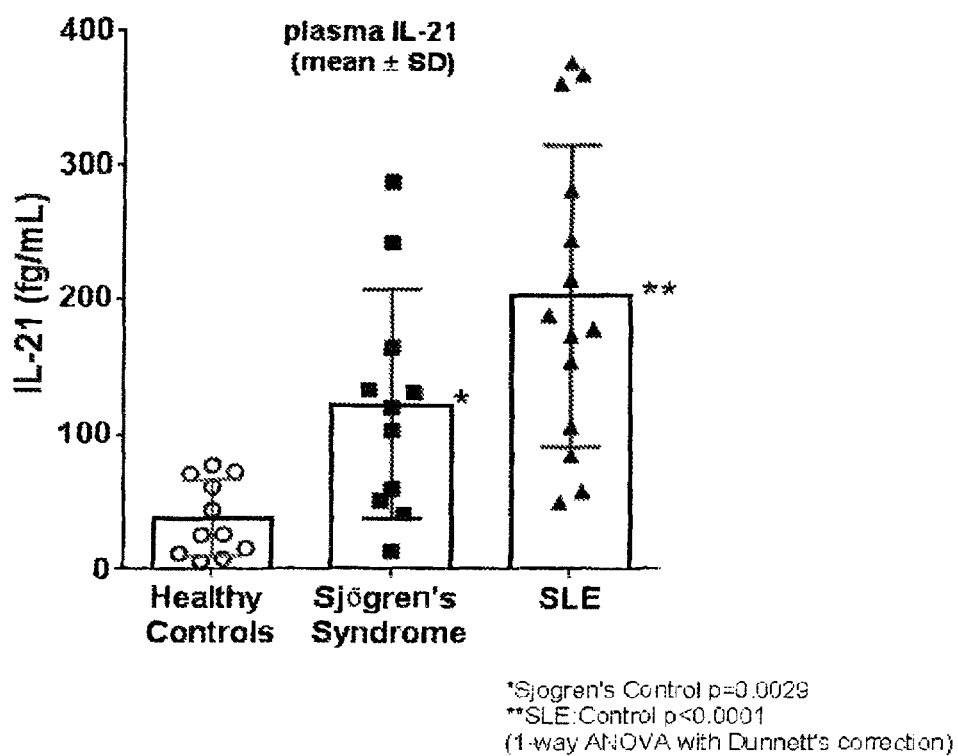

SEQUENCE LISTING

<160> NUMBER OF SEQ ID NOS: 45

<210> SEQ ID NO 1
<211> LENGTH: 11
<212> TYPE: PRT
<213> ORGANISM: Artificial Sequence
<220> FEATURE:
<223> OTHER INFORMATION: Synthetic

<400> SEQUENCE: 1

Arg Ala Ser Gln Asp Ile Ser Asn Tyr Leu Asn
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Synthetic

<400> SEQUENCE: 2

Tyr Thr Ser Arg Leu His Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

Gln Gln Phe His Thr Leu Arg Thr Phe
1               5

<210> SEQ ID NO 4
<211> LENGTH: 10
<212> TYPE: PRT
<213> ORGANISM: Artificial Sequence
<220> FEATURE:
<223> OTHER INFORMATION: Synthetic

<400> SEQUENCE: 4

Gly Tyr Thr Phe Thr Asp Tyr Trp Met His
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Synthetic

<400> SEQUENCE: 5

Leu Ile Asp Thr Ser Asp Ser Tyr Thr Ile Tyr Asn Gln Lys Phe Lys
1               5                   10                  15

Gly

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Tyr Gly Pro Leu Ala Met Asp Tyr
1               5

<210> SEQ ID NO 7
<211> LENGTH: 11
<212> TYPE: PRT
<213> ORGANISM: Artificial Sequence
<220> FEATURE:
<223> OTHER INFORMATION: Synthetic

<400> SEQUENCE: 7

Arg Ala Ser Lys Ser Ile Glu Lys Tyr Ile Ala
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Synthetic

<400> SEQUENCE: 8

Ala Gly Gly Thr Leu Gln Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic

<400> SEQUENCE: 9

Gln Gln His Glu Glu Tyr Pro Leu Thr
1               5

<210> SEQ ID NO 10
<211> LENGTH: 10
<212> TYPE: PRT
<213> ORGANISM: Artificial Sequence
<220> FEATURE:
<223> OTHER INFORMATION: Synthetic

<400> SEQUENCE: 10

Gly Tyr Asp Phe Thr Gly Tyr Thr Met Asn
1               5                   10

<210> SEQ ID NO 11
<211> LENGTH: 17
<212> TYPE: PRT
<213> ORGANISM: Artificial Sequence
<220> FEATURE:
<223> OTHER INFORMATION: Synthetic

<400> SEQUENCE: 11

Leu Ile Asn Pro Tyr Asn Gly Gly Thr Ala Tyr Ser Pro Lys Phe Lys
1               5                   10                  15

Gly

<210> SEQ ID NO 12
<211> LENGTH: 13
<212> TYPE: PRT
<213> ORGANISM: Artificial Sequence
<220> FEATURE:
<223> OTHER INFORMATION: Synthetic

<400> SEQUENCE: 12

```
Thr His Tyr Tyr Gly Ser Glu Tyr Thr Gly Met Asp Tyr
1               5                   10

<210> SEQ ID NO 13
<211> LENGTH: 16
<212> TYPE: PRT
<213> ORGANISM: Artificial Sequence
<220> FEATURE:
<223> OTHER INFORMATION: Synthetic

<400> SEQUENCE: 13

Lys Ser Ser Gln Ser Leu Leu Asp Val Asp Gly Lys Thr Tyr Leu Asn
1               5                   10                  15

<210> SEQ ID NO 14
<211> LENGTH: 7
<212> TYPE: PRT
<213> ORGANISM: Artificial Sequence
<220> FEATURE:
<223> OTHER INFORMATION: Synthetic

<400> SEQUENCE: 14

Leu Val Ser Lys Leu Asp Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic

<400> SEQUENCE: 15

Trp Gln Gly Thr His Phe Pro Tyr Thr
1               5

<210> SEQ ID NO 16
<211> LENGTH: 10
<212> TYPE: PRT
<213> ORGANISM: Artificial Sequence
<220> FEATURE:
<223> OTHER INFORMATION: Synthetic

<400> SEQUENCE: 16

Gly Tyr Phe Phe Thr Leu Tyr Met Met His
1               5                   10

<210> SEQ ID NO 17
<211> LENGTH: 17
<212> TYPE: PRT
<213> ORGANISM: Artificial Sequence
<220> FEATURE:
<223> OTHER INFORMATION: Synthetic

<400> SEQUENCE: 17

Tyr Ile Asn Pro Ser Ser Gly Tyr Thr Glu Tyr Asn Gln Lys Phe Lys
1               5                   10                  15

Asp

<210> SEQ ID NO 18
<211> LENGTH: 4
<212> TYPE: PRT
<213> ORGANISM: Artificial Sequence
<220> FEATURE:
<223> OTHER INFORMATION: Synthetic
```

<400> SEQUENCE: 18

Asp Phe Asp Tyr
1

<210> SEQ ID NO 19
<211> LENGTH: 106
<212> TYPE: PRT
<213> ORGANISM: Artificial Sequence
<220> FEATURE:
<223> OTHER INFORMATION: Synthetic

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe His Thr Leu Arg Thr
                85                  90                  95

Phe Gly Gly Gly Thr Lys Val Glu Ile Lys
            100                 105

<210> SEQ ID NO 20
<211> LENGTH: 117
<212> TYPE: PRT
<213> ORGANISM: Artificial Sequence
<220> FEATURE:
<223> OTHER INFORMATION: Synthetic

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Trp Met His Trp Val Arg Gln Ala Pro Gly Gln Gly Leu Glu Trp Met
        35                  40                  45

Gly Leu Ile Asp Thr Ser Asp Ser Tyr Thr Ile Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Gly Pro Leu Ala Met Asp Tyr Trp Gly Gln Gly Thr Leu
            100                 105                 110

Val Thr Val Ser Ser
        115

<210> SEQ ID NO 21
<211> LENGTH: 107
<212> TYPE: PRT
<213> ORGANISM: Artificial Sequence
<220> FEATURE:
<223> OTHER INFORMATION: Synthetic

<400> SEQUENCE: 21

```
Asp Ile Gln Met Asn Gln Ser Pro Ser Tyr Leu Ala Ala Ser Pro Gly
1               5                   10                  15

Glu Thr Ile Thr Ile Asn Cys Arg Ala Ser Lys Ser Ile Glu Lys Tyr
            20                  25                  30

Ile Ala Trp Tyr Gln Glu Lys Pro Gly Lys Thr Asn Lys Leu Leu Ile
        35                  40                  45

Tyr Ala Gly Gly Thr Leu Gln Ser Gly Ile Pro Ser Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Glu Glu Tyr Pro Leu
                85                  90                  95

Thr Phe Gly Ala Gly Thr Lys Leu Glu Leu Lys
            100                 105
```

<210> SEQ ID NO 22
<211> LENGTH: 122
<212> TYPE: PRT
<213> ORGANISM: Artificial Sequence
<220> FEATURE:
<223> OTHER INFORMATION: Synthetic

<400> SEQUENCE: 22

```
Gln Val Gln Leu Gln Gln Ser Gly Pro Glu Leu Val Lys Pro Gly Ala
1               5                   10                  15

Ser Met Lys Ile Ser Cys Lys Ala Ser Gly Tyr Asp Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Thr Ala Tyr Ser Pro Lys Phe
50                  55                  60

Lys Gly Lys Ala Thr Leu Thr Val Asp Lys Ser Ser Ser Thr Val Tyr
65                  70                  75                  80

Met Glu Leu Leu Ser Leu Thr Ser Glu Asp Ser Ala Val Tyr His Cys
                85                  90                  95

Ala Arg Thr His Tyr Tyr Gly Ser Glu Tyr Thr Gly Met Asp Tyr Trp
            100                 105                 110

Gly Gln Gly Thr Ser Val Thr Val Ser Ser
        115                 120
```

<210> SEQ ID NO 23
<211> LENGTH: 112
<212> TYPE: PRT
<213> ORGANISM: Artificial Sequence
<220> FEATURE:
<223> OTHER INFORMATION: Synthetic

<400> SEQUENCE: 23

```
Asp Ile Gln Val Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Val
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
50                  55                  60

Asp Arg Phe Thr Gly Ser Gly Ser Gly Thr Asp Phe Thr Leu Arg Ile
```

```
                65                  70                  75                  80
Ser Arg Val Glu Ala Glu Asp Leu Gly Val Tyr Tyr Cys Trp Gln Gly
                    85                  90                  95

Thr His Phe Pro Tyr Thr Phe Gly Gly Gly Thr Arg Leu Glu Ile Lys
                100                 105                 110

<210> SEQ ID NO 24
<211> LENGTH: 113
<212> TYPE: PRT
<213> ORGANISM: Artificial Sequence
<220> FEATURE:
<223> OTHER INFORMATION: Synthetic

<400> SEQUENCE: 24

Gln Val Gln Leu Lys Gln Ser Ala Ala Glu Leu Ala Arg Pro Gly Ala
1               5                   10                  15

Ser Val Lys Met Ser Cys Lys Ala Ser Gly Tyr Phe Phe Thr Leu Tyr
                20                  25                  30

Met Met His Trp Ala Lys Gln Arg Pro Gly Gln Asn Leu Glu Trp Ile
            35                  40                  45

Gly Tyr Ile Asn Pro Ser Ser Gly Tyr Thr Glu Tyr Asn Gln Lys Phe
        50                  55                  60

Lys Asp Lys Thr Thr Leu Thr Ala Asp Lys Ser Ser Ser Thr Ala Tyr
65                  70                  75                  80

Met Gln Leu Ser Ser Leu Thr Ser Glu Asp Ser Ala Ile Tyr Tyr Cys
                85                  90                  95

Leu Thr Asp Phe Asp Tyr Trp Gly Gln Gly Thr Ser Leu Thr Val Ser
                100                 105                 110

Ser

<210> SEQ ID NO 25
<211> LENGTH: 213
<212> TYPE: PRT
<213> ORGANISM: Artificial Sequence
<220> FEATURE:
<223> OTHER INFORMATION: Synthetic

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe His Thr Leu Arg Thr
                85                  90                  95

Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
```

```
                145                 150                 155                 160
        Ser Val Thr Glu Gln Asp Ser Lys Asp Ser Thr Tyr Ser Leu Ser Ser
                        165                 170                 175

Thr Leu Thr Leu Ser Lys Ala Asp Tyr Glu Lys His Lys Val Tyr Ala
                        180                 185                 190

Cys Glu Val Thr His Gln Gly Leu Ser Ser Pro Val Thr Lys Ser Phe
                        195                 200                 205

Asn Arg Gly Glu Cys
                        210

<210> SEQ ID NO 26
<211> LENGTH: 443
<212> TYPE: PRT
<213> ORGANISM: Artificial Sequence
<220> FEATURE:
<223> OTHER INFORMATION: Synthetic

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Trp Met His Trp Val Arg Gln Ala Pro Gly Gln Gly Leu Glu Trp Met
            35                  40                  45

Gly Leu Ile Asp Thr Ser Asp Ser Tyr Thr Ile Tyr Asn Gln Lys Phe
        50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Gly Pro Leu Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Ala Ala Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
```

```
            290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
        435                 440

<210> SEQ ID NO 27
<211> LENGTH: 214
<212> TYPE: PRT
<213> ORGANISM: Artificial Sequence
<220> FEATURE:
<223> OTHER INFORMATION: Synthetic

<400> SEQUENCE: 27

Asp Ile Gln Met Asn Gln Ser Pro Ser Tyr Leu Ala Ala Ser Pro Gly
1               5                   10                  15

Glu Thr Ile Thr Ile Asn Cys Arg Ala Ser Lys Ser Ile Glu Lys Tyr
            20                  25                  30

Ile Ala Trp Tyr Gln Glu Lys Pro Gly Lys Thr Asn Lys Leu Leu Ile
        35                  40                  45

Tyr Ala Gly Gly Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Glu Glu Tyr Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
```

<210> SEQ ID NO 28
<211> LENGTH: 446
<212> TYPE: PRT
<213> ORGANISM: Artificial Sequence
<220> FEATURE:
<223> OTHER INFORMATION: Synthetic

<400> SEQUENCE: 28

```
Gln Val Gln Leu Gln Gln Ser Gly Pro Glu Leu Val Lys Pro Gly Ala
1               5                   10                  15

Ser Met Lys Ile Ser Cys Lys Ala Ser Gly Tyr Asp Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Thr Ala Tyr Ser Pro Lys Phe
    50                  55                  60

Lys Gly Lys Ala Thr Leu Thr Val Asp Lys Ser Ser Thr Val Tyr
65                  70                  75                  80

Met Glu Leu Leu Ser Leu Thr Ser Glu Asp Ser Ala Val Tyr His Cys
                85                  90                  95

Ala Arg Thr His Tyr Tyr Gly Ser Glu Tyr Thr Gly Met Asp Tyr Trp
            100                 105                 110

Gly Gln Gly Thr Ser Val Thr Val Ser Ser Ala Lys Thr Thr Pro Pro
        115                 120                 125

Ser Val Tyr Pro Leu Ala Pro Gly Ser Ala Ala Gln Thr Asn Ser Met
    130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
            180                 185                 190

Pro Ser Ser Thr Trp Pro Ser Glu Thr Val Thr Cys Asn Val Ala His
        195                 200                 205

Pro Ala Ser Ser Thr Lys Val Asp Lys Lys Ile Val Pro Arg Asp Cys
    210                 215                 220

Gly Cys Lys Pro Cys Ile Cys Thr Val Pro Glu Val Ser Ser Val Phe
225                 230                 235                 240

Ile Phe Pro Pro Lys Pro Lys Asp Val Leu Thr Ile Thr Leu Thr Pro
                245                 250                 255

Lys Val Thr Cys Val Val Val Asp Ile Ser Lys Asp Asp Pro Glu Val
            260                 265                 270

Gln Phe Ser Trp Phe Val Asp Asp Val Glu Val His Thr Ala Gln Thr
        275                 280                 285

Gln Pro Arg Glu Glu Gln Phe Asn Ser Thr Phe Arg Ser Val Ser Glu
    290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
                325                 330                 335

Lys Thr Lys Gly Arg Pro Lys Ala Pro Gln Val Tyr Thr Ile Pro Pro
            340                 345                 350

Pro Lys Glu Gln Met Ala Lys Asp Lys Val Ser Leu Thr Cys Met Ile
```

```
                      355                 360                 365
Thr Asp Phe Phe Pro Glu Asp Ile Thr Val Glu Trp Gln Trp Asn Gly
370                 375                 380

Gln Pro Ala Glu Asn Tyr Lys Asn Thr Gln Pro Ile Met Asp Thr Asp
385                 390                 395                 400

Gly Ser Tyr Phe Val Tyr Ser Lys Leu Asn Val Gln Lys Ser Asn Trp
                405                 410                 415

Glu Ala Gly Asn Thr Phe Thr Cys Ser Val Leu His Glu Gly Leu His
            420                 425                 430

Asn His His Thr Glu Lys Ser Leu Ser His Ser Pro Gly Lys
        435                 440                 445

<210> SEQ ID NO 29
<211> LENGTH: 219
<212> TYPE: PRT
<213> ORGANISM: Artificial Sequence
<220> FEATURE:
<223> OTHER INFORMATION: Synthetic

<400> SEQUENCE: 29

Asp Ile Gln Val Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Val
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
50                  55                  60

Asp Arg Phe Thr Gly Ser Gly Ser Gly Thr Asp Phe Thr Leu Arg Ile
65                  70                  75                  80

Ser Arg Val Glu Ala Glu Asp Leu Gly Val Tyr Tyr Cys Trp Gln Gly
                85                  90                  95

Thr His Phe Pro Tyr Thr Phe Gly Gly Gly Thr Arg Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 30
<211> LENGTH: 437
<212> TYPE: PRT
<213> ORGANISM: Artificial Sequence
<220> FEATURE:
<223> OTHER INFORMATION: Synthetic

<400> SEQUENCE: 30
```

-continued

```
Gln Val Gln Leu Lys Gln Ser Ala Ala Glu Leu Ala Arg Pro Gly Ala
1               5                   10                  15

Ser Val Lys Met Ser Cys Lys Ala Ser Gly Tyr Phe Thr Leu Tyr
            20                  25                  30

Met Met His Trp Ala Lys Gln Arg Pro Gly Gln Asn Leu Glu Trp Ile
        35                  40                  45

Gly Tyr Ile Asn Pro Ser Ser Gly Tyr Thr Glu Tyr Asn Gln Lys Phe
    50                  55                  60

Lys Asp Lys Thr Thr Leu Thr Ala Asp Lys Ser Ser Ser Thr Ala Tyr
65                  70                  75                  80

Met Gln Leu Ser Ser Leu Thr Ser Glu Asp Ser Ala Ile Tyr Tyr Cys
            85                  90                  95

Leu Thr Asp Phe Asp Tyr Trp Gly Gln Gly Thr Ser Leu Thr Val Ser
            100                 105                 110

Ser Ala Lys Thr Thr Pro Pro Ser Val Tyr Pro Leu Ala Pro Gly Ser
            115                 120                 125

Ala Ala Gln Thr Asn Ser Met Val Thr Leu Gly Cys Leu Val Lys Gly
            130                 135                 140

Tyr Phe Pro Glu Pro Val Thr Val Thr Trp Asn Ser Gly Ser Leu Ser
145                 150                 155                 160

Ser Gly Val His Thr Phe Pro Ala Val Leu Gln Ser Asp Leu Tyr Thr
                165                 170                 175

Leu Ser Ser Ser Val Thr Val Pro Ser Ser Thr Trp Pro Ser Glu Thr
                180                 185                 190

Val Thr Cys Asn Val Ala His Pro Ala Ser Ser Thr Lys Val Asp Lys
            195                 200                 205

Lys Ile Val Pro Arg Asp Cys Gly Cys Lys Pro Cys Ile Cys Thr Val
        210                 215                 220

Pro Glu Val Ser Ser Val Phe Ile Phe Pro Pro Lys Pro Lys Asp Val
225                 230                 235                 240

Leu Thr Ile Thr Leu Thr Pro Lys Val Thr Cys Val Val Val Asp Ile
            245                 250                 255

Ser Lys Asp Asp Pro Glu Val Gln Phe Ser Trp Phe Val Asp Asp Val
        260                 265                 270

Glu Val His Thr Ala Gln Thr Gln Pro Arg Glu Glu Gln Phe Asn Ser
        275                 280                 285

Thr Phe Arg Ser Val Ser Glu Leu Pro Ile Met His Gln Asp Trp Leu
        290                 295                 300

Asn Gly Lys Glu Phe Lys Cys Arg Val Asn Ser Ala Ala Phe Pro Ala
305                 310                 315                 320

Pro Ile Glu Lys Thr Ile Ser Lys Thr Lys Gly Arg Pro Lys Ala Pro
                325                 330                 335

Gln Val Tyr Thr Ile Pro Pro Lys Glu Gln Met Ala Lys Asp Lys
                340                 345                 350

Val Ser Leu Thr Cys Met Ile Thr Asp Phe Phe Pro Glu Asp Ile Thr
            355                 360                 365

Val Glu Trp Gln Trp Asn Gly Gln Pro Ala Glu Asn Tyr Lys Asn Thr
        370                 375                 380

Gln Pro Ile Met Asp Thr Asp Gly Ser Tyr Phe Val Tyr Ser Lys Leu
385                 390                 395                 400

Asn Val Gln Lys Ser Asn Trp Glu Ala Gly Asn Thr Phe Thr Cys Ser
            405                 410                 415

Val Leu His Glu Gly Leu His Asn His His Thr Glu Lys Ser Leu Ser
```

His Ser Pro Gly Lys
     435

<210> SEQ ID NO 31
<211> LENGTH: 318
<212> TYPE: DNA
<213> ORGANISM: Artificial Sequence
<220> FEATURE:
<223> OTHER INFORMATION: Synthetic

<400> SEQUENCE: 31
gacatccaga tgacccagtc tccatcctcc ctgtctgcat ctgtaggaga cagagtcacc    60
atcacttgca gggcaagtca ggacattagc aattatttaa actggtatca gcagaaacca   120
gggaaagccc ctaagctcct gatctattac acatcaagat acactcagg ggtcccatca   180 aggttcagtg gcagtggatc tgggacagat ttcactctca ccatcagcag tctgcaacct   240
gaagattttg caacttacta ctgtcaacag tttcacacgc ttcggacgtt cggcggaggg   300
accaaggtgg agatcaaa                                                 318

<210> SEQ ID NO 32
<211> LENGTH: 351
<212> TYPE: DNA
<213> ORGANISM: Artificial Sequence
<220> FEATURE:
<223> OTHER INFORMATION: Synthetic

<400> SEQUENCE: 32
caggtgcagc tggtgcagtc tggggctgag gtgaagaagc ctggggcctc agtgaaggtt    60
tcctgcaagg catctggcta cacattcact gactactgga tgcactgggt gcgacaggcc   120
cctggacaag gcttgagtg gatgggactg attgatactt ctgatagtta tactatctac   180
aatcaaaagt tcaagggcag agtcaccatg accaggggaca cgtccacgag cacagtctac   240
atggagctga gcagcctgag atctgaggac acggccgtgt attactgtgc aagatatggg   300
cccctggcta tggactactg gggccagggc accctggtca ccgtctcctc a            351

<210> SEQ ID NO 33
<211> LENGTH: 639
<212> TYPE: DNA
<213> ORGANISM: Artificial Sequence
<220> FEATURE:
<223> OTHER INFORMATION: Synthetic

<400> SEQUENCE: 33
gacatccaga tgacccagtc tccatcctcc ctgtctgcat ctgtaggaga cagagtcacc    60
atcacttgca gggcaagtca ggacattagc aattatttaa actggtatca gcagaaacca   120
gggaaagccc ctaagctcct gatctattac acatcaagat acactcagg ggtcccatca   180 aggttcagtg gcagtggatc tgggacagat ttcactctca ccatcagcag tctgcaacct   240
gaagattttg caacttacta ctgtcaacag tttcacacgc ttcggacgtt cggcggaggg   300
accaaggtgg agatcaaaag aactgtggcg gcgccatctg tcttcatctt cccgccatct   360
gatgagcagt tgaaatccgg aactgcctct gttgtgtgcc tgctgaataa cttctatccc   420
agagaggcca agtacagtg gaaggtggat aacgccctcc aatcgggtaa ctcccaggag   480
agtgtcacag agcaggacag caaggacagc acctacagcc tcagcagcac cctgacgctg   540
agcaaagcag actacgagaa acacaaagtc tacgcctgcg aagtcaccca tcagggcctg   600
agctcgcccg tcacaaagag cttcaacagg ggagagtgc         639

<210> SEQ ID NO 34
<211> LENGTH: 1329
<212> TYPE: DNA
<213> ORGANISM: Artificial Sequence
<220> FEATURE:
<223> OTHER INFORMATION: Synthetic

<400> SEQUENCE: 34
caggtgcagc tggtgcagtc tggggctgag gtgaagaagc ctggggcctc agtgaaggtt    60
tcctgcaagg catctggcta cacattcact gactactgga tgcactgggt gcgacaggcc   120
cctggacaag ggcttgagtg gatgggactg attgatactt ctgatagtta tactatctac   180
aatcaaaagt tcaagggcag agtcaccatg accagggaca cgtccacgag cacagtctac   240
atggagctga gcagcctgag atctgaggac acggccgtgt attactgtgc aagatatggg   300
cccctggcta tggactactg gggccagggc accctggtca ccgtctcctc agcctccacc   360
aagggcccat cggtcttccc gctagcgccc tgctccagga gcacctccga gagcacagcc   420
gccctgggct gcctggtcaa ggactacttc cccgaaccgg tgacggtgtc gtggaactca   480
ggcgccctga ccagcggcgt gcacaccttc ccggctgtcc tacagtcctc aggactctac   540
tccctcagca gcgtggtgac cgtgccctcc agcagcttgg gcacgaagac ctacacctgc   600
aacgtagatc acaagcccag caacaccaag gtggacaaga gagttgagtc caaatatggt   660
cccccatgcc caccctgccc agcacctgag gccgcgggg gaccatcagt cttcctgttc   720
cccccaaaac ccaaggacac tctcatgatc tcccggaccc ctgaggtcac gtgcgtggtg   780
gtggacgtga gccaggaaga cccgaggtc cagttcaact ggtacgtgga tggcgtggag   840
gtgcataatg ccaagacaaa gccgcgggag gagcagttca acagcacgta ccgtgtggtc   900
agcgtcctca ccgtcctgca ccaggactgg ctgaacggca aggagtacaa gtgcaaggtc   960
tccaacaaag gcctcccgtc ctccatcgag aaaaccatct ccaaagccaa agggcagccc  1020
cgagagccac aggtgtacac cctgccccca tcccaggagg agatgaccaa gaaccaggtc  1080
agcctgacct gcctggtcaa aggcttctac cccagcgaca tcgccgtgga gtgggaaagc  1140
aatgggcagc cggagaacaa ctacaagacc acgcctcccg tgctggactc cgacggctcc  1200
ttcttcctct acagcaggct aaccgtggac aagagcaggt ggcaggaggg gaatgtcttc  1260
tcatgctccg tgatgcatga ggctctgcac aaccactaca cacagaagag cctctccctg  1320
tctctgggt                                                          1329

<210> SEQ ID NO 35
<211> LENGTH: 321
<212> TYPE: DNA
<213> ORGANISM: Artificial Sequence
<220> FEATURE:
<223> OTHER INFORMATION: Synthetic

<400> SEQUENCE: 35
gacatccaga tgaaccagtc tccatcttat cttgctgcat ctcctggaga aaccattact    60
attaattgca gggcaagtaa gagcattgag aaatatatcg cctggtatca agagaaacct   120
gggaaaacta ataagcttct tatctacgca ggaggcactt tgcaatctgg aattccatca   180
aggttcagtg gcagtggatc tggtacagat ttcactctca ccatcagtag cctggagcct   240
gaagattttg caatgtatta ctgtcaacag catgaggaat accgctcac gttcggtgct   300
gggaccaagc tggagctgaa a                                             321

<210> SEQ ID NO 36
<211> LENGTH: 366
<212> TYPE: DNA
<213> ORGANISM: Artificial Sequence
<220> FEATURE:
<223> OTHER INFORMATION: Synthetic

<400> SEQUENCE: 36

| | | | | | |
|---|---|---|---|---|---|
| caggtccagc | tgcagcagtc | tggacctgag | ctggtgaagc | ctggagcttc | aatgaagata | 60 |
| tcctgcaagg | cttctggtta | cgacttcact | ggctacacca | tgaactgggt | gaagcagagc | 120 |
| catggaaaga | accttgagtg | gattggactt | attaatcctt | acaatggtgg | tactgcctac | 180 |
| agccctaagt | tcaagggcaa | ggccacatta | actgtagaca | agtcatccag | cacagtctac | 240 |
| atggagctcc | tcagtctgac | atctgaggac | tctgcagtct | atcactgtgc | aaggactcac | 300 |
| tactacggaa | gtgaatacac | tggtatggac | tactggggtc | aaggaacctc | agtcaccgtc | 360 |
| tcctca | | | | | | 366 |

<210> SEQ ID NO 37
<211> LENGTH: 642
<212> TYPE: DNA
<213> ORGANISM: Artificial Sequence
<220> FEATURE:
<223> OTHER INFORMATION: Synthetic

<400> SEQUENCE: 37

| | | | | | |
|---|---|---|---|---|---|
| gacatccaga | tgaaccagtc | tccatcttat | cttgctgcat | ctcctggaga | aaccattact | 60 |
| attaattgca | gggcaagtaa | gagcattgag | aaatatatcg | cctggtatca | agagaaacct | 120 |
| gggaaaacta | taagcttcct | tatctacgca | ggaggcactt | tgcaatctgg | aattccatca | 180 |
| aggttcagtg | gcagtggatc | tggtacagat | ttcactctca | ccatcagtag | cctggagcct | 240 |
| gaagattttg | caatgtatta | ctgtcaacag | catgaggaat | acccgctcac | gttcggtgct | 300 |
| gggaccaagc | tggagctgaa | acgggctgat | gcggcgccca | ctgtatccat | cttcccacca | 360 |
| tccagtgagc | agttaacatc | tggaggtgct | agcgtcgtgt | gcttcttgaa | caacttctac | 420 |
| cccaaagaca | tcaatgtcaa | gtggaagatt | gatggcagtg | aacgacaaaa | tggcgtcctg | 480 |
| aacagttgga | ctgatcagga | cagcaaagac | agcacctaca | gcatgagcag | cacccctcacg | 540 |
| ttgaccaagg | acgagtatga | acgacataac | agctatacct | gtgaggccac | tcacaagaca | 600 |
| tcaacttcac | ccattgtcaa | gagcttcaac | aggaatgagt | gt | | 642 |

<210> SEQ ID NO 38
<211> LENGTH: 1338
<212> TYPE: DNA
<213> ORGANISM: Artificial Sequence
<220> FEATURE:
<223> OTHER INFORMATION: Synthetic

<400> SEQUENCE: 38

| | | | | | |
|---|---|---|---|---|---|
| caggtccagc | tgcagcagtc | tggacctgag | ctggtgaagc | ctggagcttc | aatgaagata | 60 |
| tcctgcaagg | cttctggtta | cgacttcact | ggctacacca | tgaactgggt | gaagcagagc | 120 |
| catggaaaga | accttgagtg | gattggactt | attaatcctt | acaatggtgg | tactgcctac | 180 |
| agccctaagt | tcaagggcaa | ggccacatta | actgtagaca | agtcatccag | cacagtctac | 240 |
| atggagctcc | tcagtctgac | atctgaggac | tctgcagtct | atcactgtgc | aaggactcac | 300 |
| tactacggaa | gtgaatacac | tggtatggac | tactggggtc | aaggaacctc | agtcaccgtc | 360 |

```
tcctcagcca aaacgacacc cccatctgtc tatccgctag cccctggatc tgccgcccag    420
accaacagca tggtgaccct gggctgtctg gtgaagggct acttccctga gcctgtgaca    480
gtgacctgga acagcggctc tctgtctagc ggcgtgcaca cattccctgc cgtgctgcag    540
agcgacctgt acaccctgag cagcagcgtg accgtgccta gcagcacatg gcctagcgag    600
accgtgacat gcaacgtggc ccaccctgcc tcttctacca aggtggacaa gaagatcgtg    660
cccagagact gcggctgcaa gccttgcatc tgcaccgtgc ctgaggtgag cagcgtgttc    720
atcttcccac ccaagcccaa ggacgtgctc accatcaccc tcaccccaa ggtcacgtgt    780 gttgtggtag acatcagcaa ggatgatccc gaggtccagt tcagctggtt tgtagatgat    840
gtggaggtgc acacagctca gacgcaaccc cgggaggagc agttcaacag cactttccgc    900
tcagtcagtg aacttcccat catgcaccag gactggctca atggcaagga gttcaaatgc    960
agggtcaaca gtgcagcttt ccctgccccc atcgagaaaa ccatctccaa aaccaaaggc   1020
agaccgaagg ctccacaggt gtacaccatt ccacctccca aggagcagat ggccaaggat   1080
aaagtcagtc tgacctgcat gataacagac ttcttccctg aagacattac tgtggagtgg   1140
cagtggaatg ggcagccagc ggagaactac aagaacactc agcccatcat ggacacagat   1200
ggctcttact tcgtctacag caagctcaat gtgcagaaga gcaactggga ggcaggaaat   1260
actttcacct gctctgtgtt acatgagggc ctgcacaacc accatactga gaagagcctc   1320
tcccactctc ctggtaaa                                                 1338

<210> SEQ ID NO 39
<211> LENGTH: 336
<212> TYPE: DNA
<213> ORGANISM: Artificial Sequence
<220> FEATURE:
<223> OTHER INFORMATION: Synthetic

<400> SEQUENCE: 39
gacatccagg tgactcagac tccactcact ttgtcggtta ccattggaca accagcctcc     60
atctcttgca agtcaagtca gagcctctta gatgtggatg gaaagacata tttgaattgg    120
ttgttacaga ggccaggcca gtctccaaag cgcctaatct atctggtgtc taaactggac    180
tctggagtcc ctgacaggtt cactggcagt ggatcaggga cagatttcac actgagaatc    240
agcagagtgg aggctgagga tttgggagtt tattattgct ggcaaggtac acattttcct    300
tacacgttcg gaggggggac cagactggaa ataaaa                             336

<210> SEQ ID NO 40
<211> LENGTH: 339
<212> TYPE: DNA
<213> ORGANISM: Artificial Sequence
<220> FEATURE:
<223> OTHER INFORMATION: Synthetic

<400> SEQUENCE: 40
caggtgcagc tgaagcagtc tgcagctgaa ctggcaagac ctggggcctc agtgaagatg     60
tcctgcaagg cttctggcta tttttttacc ctgtacatga tgcactgggc aaaacagagg    120
cctggacaga tctgaatg gattggatac attaatccta gcagtggata tactgaatac    180
aatcagaagt tcaaggacaa gaccacattg actgcagaca aatcctccag cacagcctac    240
atgcaactga gcagcctgac atctgaggat tctgcgatct attactgtct aacggacttt    300
gactactggg gccaaggcac cagtctcaca gtctcctca                          339
```

<210> SEQ ID NO 41
<211> LENGTH: 657
<212> TYPE: DNA
<213> ORGANISM: Artificial Sequence
<220> FEATURE:
<223> OTHER INFORMATION: Synthetic

<400> SEQUENCE: 41

```
gacatccagg tgactcagac tccactcact ttgtcggtta ccattggaca accagcctcc      60
atctcttgca agtcaagtca gagcctctta gatgtggatg aaagacata  tttgaattgg     120
ttgttacaga ggccaggcca gtctccaaag cgcctaatct atctggtgtc taaactggac     180
tctggagtcc ctgacaggtt cactggcagt ggatcaggga cagatttcac actgagaatc     240
agcagagtgg aggctgagga tttggagtt  tattattgct ggcaaggtac acattttcct     300
tacacgttcg gaggggggac cagactggaa ataaaacggg ctgatgctgc gcccactgta     360
tccatcttcc caccatccag tgagcagtta acatctggag gtgctagcgt cgtgtgcttc     420
ttgaacaact tctaccccaa agacatcaat gtcaagtgga gattgatgg  cagtgaacga     480
caaaatggcg tcctgaacag ttggactgat caggacagca agacagcac  ctacagcatg     540
agcagcaccc tcacgttgac caaggacgag tatgaacgac ataacagcta tacctgtgag     600
gccactcaca agacatcaac ttcacccatt gtcaagagct caacaggaa  tgagtgt        657
```

<210> SEQ ID NO 42
<211> LENGTH: 1311
<212> TYPE: DNA
<213> ORGANISM: Artificial Sequence
<220> FEATURE:
<223> OTHER INFORMATION: Synthetic

<400> SEQUENCE: 42

```
caggtgcagc tgaagcagtc tgcagctgaa ctggcaagac ctggggcctc agtgaagatg      60
tcctgcaagg cttctggcta tttttttacc ctgtacatga tgcactgggc aaaacagagg     120
cctggacaga atctggaatg gattggatac attaatccta gcagtggata tactgaatac     180
aatcagaagt tcaaggacaa gaccacattg actgcagaca atcctccag  cacagcctac     240
atgcaactga gcagcctgac atctgaggat tctgcgatct attactgtct aacggacttt     300
gactactggg gccaaggcac cagtctcaca gtctcctcag ccaaaacgac accccatct     360
gtctatccgc tagcccctgg atctgccgcc cagaccaaca gcatggtgac cctgggctgt     420
ctggtgaagg gctacttccc tgagcctgtg acagtgacct ggaacagcgg ctctctgtct     480
agcggcgtgc acacattccc tgccgtgctg cagagcgacc tgtacaccct gagcagcagc     540
gtgaccgtgc ctagcagcac atggcctagc gagaccgtga catgcaacgt ggcccaccct     600
gcctcttcta ccaaggtgga caagaagatc gtgcccagag actgcggctg caagccttgc     660
atctgcaccg tgcctgaggt gagcagcgtg ttcatcttcc cacccaagcc caaggacgtg     720
ctcaccatca ccctcacccc caaggtcacg tgtgttgtgg tagacatcag caaggatgat     780
cccgaggtcc agttcagctg gtttgtagat gatgtggagg tgcacacagc tcagacgcaa     840
ccccgggagg agcagttcaa cagcactttc cgctcagtca gtgaacttcc catcatgcac     900
caggactggc tcaatggcaa ggagttcaaa tgcagggtca acagtgcagc tttccctgcc     960
cccatcgaga aaaccatctc caaaaccaaa ggcagaccga aggctccaca ggtgtacacc    1020
attccacctc ccaaggagca gatggccaag gataaagtca gtctgacctg catgataaca    1080
gacttcttcc ctgaagacat tactgtggag tggcagtgga atgggcagcc agcggagaac    1140
```

```
tacaagaaca ctcagcccat catggacaca gatggctctt acttcgtcta cagcaagctc    1200
aatgtgcaga agagcaactg ggaggcagga aatactttca cctgctctgt gttacatgag    1260
ggcctgcaca accaccatac tgagaagagc ctctcccact ctcctggtaa a             1311
```

<210> SEQ ID NO 43
<211> LENGTH: 162
<212> TYPE: PRT
<213> ORGANISM: Homo sapiens

<400> SEQUENCE: 43

```
Met Arg Ser Ser Pro Gly Asn Met Glu Arg Ile Val Ile Cys Leu Met
1               5                   10                  15

Val Ile Phe Leu Gly Thr Leu Val His Lys Ser Ser Gln Gly Gln
            20                  25                  30

Asp Arg His Met Ile Arg Met Arg Gln Leu Ile Asp Ile Val Asp Gln
            35                  40                  45

Leu Lys Asn Tyr Val Asn Asp Leu Val Pro Glu Phe Leu Pro Ala Pro
    50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
            100                 105                 110

Gly Arg Arg Gln Lys His Arg Leu Thr Cys Pro Ser Cys Asp Ser Tyr
            115                 120                 125

Glu Lys Lys Pro Pro Lys Glu Phe Leu Glu Arg Phe Lys Ser Leu Leu
    130                 135                 140

Gln Lys Met Ile His Gln His Leu Ser Ser Arg Thr His Gly Ser Glu
145                 150                 155                 160

Asp Ser
```

<210> SEQ ID NO 44
<211> LENGTH: 132
<212> TYPE: PRT
<213> ORGANISM: Artificial Sequence
<220> FEATURE:
<223> OTHER INFORMATION: Synthetic

<400> SEQUENCE: 44

```
Met Gln Asp Arg His Met Ile Arg Met Arg Gln Leu Ile Asp Ile Val
1               5                   10                  15

Asp Gln Leu Lys Asn Tyr Val Asn Asp Leu Val Pro Glu Phe Leu Pro
            20                  25                  30

Ala Pro Glu Asp Val Glu Thr Asn Cys Glu Trp Ser Ala Phe Ser Cys
            35                  40                  45

Phe Gln Lys Ala Gln Leu Lys Ser Ala Asn Thr Gly Asn Asn Glu Arg
    50                  55                  60

Ile Ile Asn Val Ser Ile Lys Lys Leu Lys Arg Lys Pro Pro Ser Thr
65                  70                  75                  80

Asn Ala Gly Arg Arg Gln Lys His Arg Leu Thr Cys Pro Ser Cys Asp
                85                  90                  95

Ser Tyr Glu Lys Lys Pro Pro Lys Glu Phe Leu Glu Arg Phe Lys Ser
            100                 105                 110

Leu Leu Gln Lys Met Ile His Gln His Leu Ser Ser Arg Thr His Gly
            115                 120                 125
```

<210> SEQ ID NO 45
<211> LENGTH: 489
<212> TYPE: DNA
<213> ORGANISM: Homo sapiens

<400> SEQUENCE: 45

```
atgagatcca gtcctggcaa catggagagg attgtcatct gtctgatggt catcttcttg    60
gggacactgg tccacaaatc aagctcccaa ggtcaagatc gccacatgat tagaatgcgt   120
caacttatag atattgttga tcagctgaaa aattatgtga atgacttggt ccctgaattt   180
ctgccagctc cagaagatgt agagacaaac tgtgagtggt cagcttttc ctgctttcag   240
aaggcccaac taaagtcagc aaatacagga acaatgaaa ggataatcaa tgtatcaatt   300
aaaaagctga agaggaaacc accttccaca aatgcaggga aagacagaa acacagacta   360
acatgccctt catgtgattc ttatgagaaa aaaccaccca aagaattcct agaaagattc   420
aaatcacttc tccaaaagat gattcatcag catctgtcct ctagaacaca cggaagtgaa   480
gattcctga                                                          489
```

METHODS OF DETECTING HUMAN IL-21

The present invention relates to the field of medicine. More specifically, the present invention relates to antibodies that bind human interleukin-21 (IL-21) to form a detectable IL-21/anti-IL-21 antibody complex useful in determination of IL-21 levels found in human biological matrices with high sensitivity (sub picogram per milliliter (pg/ml)). In particular, the present invention relates to determination of femtogram per milliliter levels of IL-21 in vitro assays.

IL-21 is an important cytokine involved in the pathogenesis of inflammatory diseases, including allergic diseases, cancer, and autoimmune diseases, particularly, psoriasis, systemic lupus erythematosus (SLE), chronic inflammatory bowel disease and Sjögren's syndrome. Elevated serum levels of IL-21 are reportedly associated with disease severity in patients with autoimmune diseases such as psoriasis, SLE or Sjögren's syndrome. An enzyme-linked immunosorbent assay (ELISA) kit for detecting human IL-21 is commercially available, but it has a low limit of detection of 16 pg/mL (Weir et al. Cytokine 60 (2012) 220-225). The kit is, however, unable to detect the true level of IL-21 in patient samples.

There is, therefore, a need for anti-IL-21 antibodies that possess higher binding affinity and selectivity to human IL-21 resulting in enhanced sensitivity in IL-21 determinations, or, when used in ELISA assays, provide minimal interference and broad dilutional linearity. Preferably, the antibodies are monoclonal antibodies, and include, for example, two or more distinct antibodies that recognize two or more distinct epitopes on IL-21 so that a pair of antibodies can bind simultaneously to IL-21 in an assay.

There is a need for anti-IL-21 antibodies that bind IL-21, which permits diagnostic assessment of IL-21 levels, before, during, and/or after treatment of the patient, with minimal plasma protein interference and with higher sensitivity than commercially available assays. Accordingly, the present invention seeks to provide alternative anti-IL-21 antibodies that specifically bind to human IL-21. The present invention further seeks to provide a rapid and convenient method for quantifying human IL-21 in vitro at femtogram per milliliter (fg/ml) levels.

Accordingly, a first aspect of the present invention provides an antibody, or antigen-binding fragment thereof, that binds human IL-21, comprising a light chain variable region (LCVR) and a heavy chain variable region (HCVR), wherein said LCVR comprises three light chain complementarily determining regions (LCDRs) and said HCVR comprises three heavy chain complementarity determining regions (HCDRs), wherein the amino acid sequences of said three LCDRs and said three HCDRs are selected from the group consisting of:

a)
RASQDISNYLN, (SEQ ID NO: 1)

YTSRLHS, (SEQ ID NO: 2)

QQFHTLRTF, (SEQ ID NO: 3)

GYTFTDYWMH, (SEQ ID NO: 4)

LIDTSDSYTIYNQKFKG, (SEQ ID NO: 5)
and

YGPLAMDY; (SEQ ID NO: 6)

b)
RASKSIEKYIA, (SEQ ID NO: 7)

AGGTLQS, (SEQ ID NO: 8)

QQHEEYPLT; (SEQ ID NO: 9)

GYDFTGYTMN, (SEQ ID NO: 10)

LINPYNGGTAYSPKFKG, (SEQ ID NO: 11)
and

THYYGSEYTGMDY; (SEQ ID NO: 12)
and c)
KSSQSLLDVDGKTYLN, (SEQ ID NO: 13)

LVSKLDS, (SEQ ID NO: 14)

WQGTHFPYT, (SEQ ID NO: 15)

GYFFTLYMMH, (SEQ ID NO: 16)

YINPSSGYTEYNQKFKD, (SEQ ID NO: 17)
and

DFDY. (SEQ ID NO: 18)

In a further embodiment, the present invention provides an antibody, or antigen-binding fragment thereof, that binds human IL-21, wherein said antibody or antigen-binding fragment thereof comprises a LCVR and a HCVR, wherein the amino acid sequences of said LCVR and said HCVR are selected from the group consisting of
a) the amino sequence of SEQ ID NO: 19 and the amino sequence of SEQ ID NO: 20;
b) the amino sequence of SEQ ID NO: 21 and the amino sequence of SEQ ID NO: 22; and
c) the amino sequence of SEQ ID NO: 23 and the amino sequence of SEQ ID NO: 24.

In another embodiment, the present invention provides an antibody that binds human IL-21, wherein said antibody comprises a light chain and a heavy chain, wherein the amino acid sequences of said light chain and said heavy chain are selected from the group consisting of:
a) the amino sequence of SEQ ID NO:25 and the amino sequence of SEQ NO:26;
b) the amino sequence of SEQ ID NO:27 and the amino sequence of SEQ ID NO: 28; and
c) the amino sequence of SEQ ID NO:29 and the amino sequence of SEQ ID NO:30.

In another embodiment, the present invention provides an antibody that binds human IL-21, wherein said antibody comprises two light chains and two heavy chains, wherein the amino acid sequences of each of said light chains and each of said heavy chains are selected from the group consisting of:

a) the amino sequence of SEQ ID NO:25 and the amino sequence of SEQ ID NO:26;
b) the amino sequence of SEQ IO NO:27 and the amino sequence of SEQ ID NO:28; and
c) the amino sequence of SEQ ID NO:29 and the amino sequence of SEQ ID NO:30.

The present invention also provides a polynucleotide comprising a nucleotide sequence encoding the LCVR and/or the HCVR, or the light chain and/or the heavy chain of the antibodies of the present invention, wherein said polynucleotide has the nucleotide sequence as shown in SEQ ID NOs: 31, 32, 33, 34, 35, 36, 37, 38, 39, 40, 41, or 42.

The present invention also provides a recombinant expression vector comprising a polynucleotide encoding the LCVR and/or the HCVR, or the light chain and/or the heavy chain of the antibodies of the present invention.

In another embodiment, the present invention provides a host cell which has been transformed by an expression vector comprising a polynucleotide encoding the LCVR and/or the HCVR, or the light chain and/or the heavy chain of the antibodies of the present invention.

In another embodiment, the present invention further provides an antibody or antigen-binding fragment comprising a detectable label, wherein said detectable label is selected from the group consisting of a chromophore, a chromogen, a dye, a fluorescent agent, a fluorogenic agent, a phosphorescent agent, a chemiluminescent agent, a bioluminescent agent, a radionuclide, a positron emission tomography-imageable agent, and a magnetic resonance-imageable agent.

In another embodiment, the present invention provides a composition comprising an antibody or antigen-binding fragment thereof of the present invention, and an acceptable carrier, diluent, or excipient.

In another embodiment, the present invention provides an in vitro method of detecting or quantifying human IL-21 in a sample of tissue or body fluid comprising: contacting said sample with said antibody or antigen-binding fragment thereof of the present invention; optionally, removing any non-specifically bound antibody or antigen-binding fragment thereof; and detecting or quantifying the amount of the antibody or antigen-binding fragment thereof, which is specifically bound to human IL-21 in said sample quantitatively, semi-quantitatively or qualitatively.

In another aspect, the present invention provides an antibody or antigen-binding fragment thereof of the present invention for use in diagnostic, prognostic, and/or patient monitoring procedure in vitro.

In another aspect, the present invention provides a kit for use in in vitro detecting or quantifying human IL-21 in a sample of tissue or body fluid, comprising
a) a first reagent, wherein said first reagent is an antibody or antigen-binding fragment thereof, comprising a LCVR having the amino sequence of SEQ ID NO: 21 and a HCVR having the amino sequence of SEQ ID NO: 22; and
b) a second reagent, wherein said second reagent is an antibody or antigen-binding fragment comprising a LCVR having the amino sequence of SEQ ID NO: 19 and a HCVR having the amino sequence of SEQ ID NO: 20.

Preferably, the sample of tissue or body fluid is a plasma sample or a serum sample.

According to yet another aspect of the present invention, there is provided an antibody according to the present invention for use in in vitro measurement of the amount of IL-21 in a human sample.

As used herein, the term "IL-21" (also known as interleukin-21) means a type I cytokine that exerts pleiotropic effects on both innate and adaptive immune responses. IL-21 is produced by activated CD4 positive T cells including, follicular T helper and Th17 cells. The amino acid and cDNA sequences of human IL-21 are listed as SEQ ID NOs:43 and 45, respectively.

An antibody or a full-length antibody is an immunoglobulin molecule comprising two heavy chains and two light chains interconnected by disulfide bonds. The amino terminal portion of each chain includes a variable region of about 100-110 amino acids primarily responsible for antigen recognition via the complementarity determining regions (CDRs) contained therein. The carboxy-terminal portion of each chain defines a constant region primarily responsible for effector function. The antibodies of the present invention are monoclonal antibodies ("mAbs"). Monoclonal antibodies can be produced, for example, by hybridoma technologies, e.g. CDR-grafting, or combinations of such or other technologies known in the art. In another embodiment of the present invention, there is provided an antibody, or the nucleic acid encoding the same, in isolated form. As used herein, the term "isolated" refers to a protein, peptide or nucleic acid that is not found in nature and is free or substantially free from other macromolecular species found in a cellular environment. "Substantially free", as used herein, means the protein, peptide or nucleic acid of interest comprises more than 80% (on a molar basis) of the macromolecular species present, preferably more than 90% and more preferably more than 95%.

"Antigen-binding fragment", as used herein, refers to antigen-binding fragments of antibodies, i.e. antibody fragments that retain the ability to bind specifically to the antigen bound by the full-length antibody. Examples of antigen-binding fragment include, but are not limited to, Fab fragments, Fab' fragments, F(ab')$_2$ fragments, and single chain Fv fragments. Preferably, the antibody fragment is a Fab fragment.

The CDRs are interspersed with regions that are more conserved, termed framework regions ("FR"). Each light chain variable region (LCVR) and heavy chain variable region (HCVR) is composed of 3 CDRs and 4 FRs, arranged from amino-terminus to carboxy-terminus in the following order: FR1, CDR1, FR2, CDR2, FR3, CDR3, FR4. The 3 CDRs of the light chain are referred to as "LCDR1, LCDR2, and LCDR3" and the 3 CDRs of the heavy chain are referred to as "HCDR1, HCDR2, and HCDR3". The CDRs contain most of the residues which form specific interactions with the antigen. Three systems of CDR assignments for antibodies are commonly used for sequence delineation. The Kabat CDR definition (Kabat et al., "Sequences of Proteins of Immunological Interest," National Institutes of Health, Bethesda, Md. (1991)) is based upon antibody sequence variability. The Chothia CDR definition (Chothia et al., "Canonical structures for the hypervariable regions of immunoglobulins", Journal of Molecular Biology, 196, 901-917 (1987) Al-Lazikani et al., "Standard conformations for the canonical structures of immunoglobulins", Journal of Molecular Biology, 273, 927-948 (1997)) is based on three-dimensional structures of antibodies and topologies of the CDR loops. The Chothia CDR definitions are identical to the Kabat CDR definitions with the exception of HCDR1 and HCDR2. The North CDR definition (North et al., "A New Clustering of Antibody CDR Loop Conformations", Journal of Molecular Biology, 406, 228-256 (2011)) is based on affinity propagation clustering with a large number of crystal structures. The Kabat CDR definition is used in the present invention except HCDR1, which is defined with Kabat and Chothia.

Another aspect of the present invention pertains to isolated nucleic acid molecules encoding any of the aforementioned anti-IL-21 antibodies, expression vectors comprising the nucleic acid molecules, and host cells comprising the nucleic acid molecules. Additionally, the present invention provides expression vectors containing the polynucleotide sequences previously described operably linked to a control sequence such as an expression sequence, a promoter and/or an enhancer sequence. A variety of expression vectors for the efficient synthesis of antibody polypeptide in prokaryotic systems, such as bacteria and eukaryotic systems, including but not limited to, yeast and mammalian cell culture systems have been developed. The vectors of the present invention can comprise segments of chromosomal, non-chromosomal and synthetic DNA sequences.

Methods for producing and purifying antibodies and antigen-binding fragments are known in the art and can be found, for example, in Harlow and Lane (1988) Antibodies, A Laboratory Manual, Cold Spring Harbor Laboratory Press, Cold Spring Harbor, N.Y., chapters 5-8 and 15, ISBN 0-87969-314-2. Antigen-binding fragments can also be prepared by conventional methods. The present invention also provides recombinant host cells containing the recombinant vectors previously described. Cell lines of particular preference are selected based on high levels of expression, constitutive expression of protein of interest and minimal contamination from host proteins. Mammalian cell lines available as hosts for expression are well known in the art and include many immortalized cell lines, such as but not limited to, COS-7 cells, Chinese Hamster Ovary (CHO) cells, Baby Hamster Kidney (BHK) cells and many others including cell lines of lymphoid origin such as lymphoma, myeloma, or hybridoma cells. Preferred host cells for transformation of vectors and expression of the antibodies of the present invention are mammalian cells, e.g., NSO cells (non-secreting (0) mouse myeloma cells), Human embryonic kidney (HEK) 293, SP20 and Chinese hamster ovary (CHO) cells and other cell lines of lymphoid origin such as lymphoma, myeloma, or hybridoma cells. Antibodies of the present invention can be expressed in cell lines other than in hybridomas. Other eukaryotic hosts, such as yeasts, can be alternatively used. The antibodies and more specifically the antigen binding fragments thereof can also be produced from prokaryotic cells such as *Escherichia coli*. Nucleic acids, which comprise a sequence encoding an antibody according to the present invention, can be used for transformation of a suitable mammalian host cell.

The present invention further provides methods of purifying any of the aforementioned anti-IL-21 antibodies. The engineered antibodies or antigen binding fragments of the present invention may be prepared and purified using known methods.

The anti-IL-21 antibodies disclosed herein are useful for diagnostic, prognostic. and/or patient monitoring procedures, by detecting the level of IL-21 present in or on cells, tissues, or organs, whether in vivo and/or in various forms of ex vivo preparations, and in bodily fluids. The term "body fluid" refers to any fluid or fluid-like material derived from the body of a normal or diseased subject, such as blood, serum, plasma, lymph, bone marrow, urine, saliva, tears, cerebrospinal fluid, milk, amniotic fluid, bile, urine, bronchial fluid, ascites fluid, pus, and any other biological fluid product. Also included within the meaning of fluid-like materials are organ or tissue extracts, and culture media in which cells or tissue preparation from a subject have been incubated. An anti-IL-21 antibody described herein can be conjugated to an enzyme and used in an enzyme-linked immunosorbent assay (ELISA). Such assays are described in detail in, for example, Butler (1994) "ELISA" (Chapter 29), In: van Oss, C. J. et al., eds., Immunochemistry, Marcel Dekker, Inc., New York, pp. 759-803. The present anti-IL-21 antibodies can also be used in radioimmunoassay and fluorescence-activated cell sorting (FACS) analysis of IL-21 expression.

As used herein, the term "contacting" refers to bringing an antibody or antigen-binding fragment thereof and an antigen or a target protein, e.g., IL-21, together in such a manner that form detectable antigen/antibody complex useful in detecting or quantifying the antigen or target protein in sample of tissue or body fluid in vitro assays. Such contacting can be accomplished in vitro, e.g., in a test tube, a microplate or the like. Alternately, "contacting" refers to mixing together an antibody or antigen-binding fragment thereof with a liquid such as serum, or plasma in vitro assays.

BRIEF DESCRIPTION OF THE DRAWING

FIG. 1 shows the results of the analysis of human normal control samples and diseased samples in the IL-21 Quanterix SIMOA™ assay.

Antibody Compositions and Methods

There are well-known methods in the art that a skilled artisan may use to form stable, detectable antigen-antibody complexes (see, e.g., Antibodies, A Laboratory Manual by Harlow and Lane (current edition), Cold Spring Harbor Laboratory Press, Cold Spring Harbor, N.Y., for conditions permitting formation of detectable antigen/antibody complexes).

The anti-IL-21 antibodies or antigen-binding fragment thereof of the present invention or the IL-21/anti-IL-21 antibody complexes described herein can be detectably labeled using any art-known means (see, e.g., Antibody Engineering Volume 2, Kontermann, Roland; Dubel, Stefan (Eds.)). Labels can be, for example, without limitation, light-emitting or light-absorbing agents, chromophores, chromogens, magnetic or iron particles, dyes, fluorescents, fluorophores, phosphorescents, chemiluminescents, bioluminescents agent, radionuclides, enzymes, positron emission tomographic-imageable agents, magnetic micro-beads, ferrofluid nanoparticles, secondary antibodies, and magnetic resonance-imageable agents.

The term "detectably labeled" means that the anti-IL-21 antibody, or antigen-binding fragment thereof of the present invention, or a complex of IL-21/anti-IL-21 antibody has attached to it, either covalently or non-covalently, a useful detectable label. In direct conjugate-labeled antibody methods, many different useful labels can be employed including, for example, prosthetic group complexes, chromophores, chromogens (color-producing substrates), dyes, fluorescent compounds, fluorogenic compounds, radioactive isotopes, paramagnetic isotopes, and compounds that can be imaged by positron emission tomography (PET) and magnetic resonance imaging (MRI). Useful radiolabels, which are detected simply by gamma counter, scintillation counter, PET scanning, or autoradiography, include $^{3}$H, $^{124}$I, $^{125}$I, $^{131}$I, $^{35}$S, and $^{14}$C. For in vivo diagnosis, radionuclides can be bound to an antibody or antigen-binding fragments either directly or indirectly using a chelating agent such as DTPA and EDTA. Examples of such radionuclides include $^{99}$Tc, $^{123}$I, $^{125}$I, $^{131}$I, $^{111}$In, $^{97}$Ru, $^{67}$Cu, $^{67}$Ga, $^{68}$Ga, $^{72}$As, $^{89}$Zr, $^{90}$Y and $^{201}$Tl. Other suitable labels are art-known or can be determined by routine experimentation. In indirect methods, a secondary antibody can be conjugated with, for example but not restricted to an enzyme or fluorescent labels. Binding of the secondary antibody to the primary antibody, which is bound to the target antigen, can then be detected by reaction with a chromogenic substrate of the enzyme under appropriate conditions to yield a detectable signal.

Colorimetric detection can be used, employing chromogenic compounds that have, or result in, chromophores with high extinction coefficients, and which are therefore easily detectable. When later exposed to its substrate under appropriate reaction conditions, the enzyme will react with the substrate to produce a chemical label that can be detected, for example, by spectrophotometric, fluorometric, or visual means.

Enzymes commonly used for this purpose include horseradish peroxidase, alkaline phosphatase, glucose-6-phosphate dehydrogenase, malate dehydrogenase, staphylococcal nuclease, delta-V-steroid isomerase, yeast alcohol dehydrogenase, α-glycerophosphate dehydrogenase, triose phosphate isomerase, asparaginase, glucose oxidase, β-galactosidase, ribonuclease, unease, catalase, glucoamylase, and acetylcholinesterase. Examples of suitable prosthetic group complexes include, e.g., without limit, streptavidin/biotin and avidin/biotin. Use of chromogens is preferred because assays employing them can be easily performed in clinical diagnostic laboratories and reviewed by a pathologist with equipment commonly available in these laboratories. Commonly used chromogens include diaminobenzidine (DAB); DAB with enhancement; 3-amino-9-ethyl carbazole (AEC); 4-chloro-1-naphthol (4-CN); Hanker-Yates reagent; alpha-naphthol pyronin; 3,3',5,5'-tetramethylbenzidine (TMB); Fast Blue BB; Fast Red TR; new fuchsin; BCIP-NBT; tetrazolium; tetranitoblue tetrazolium (TNBT); and immunogold with silver enhancement.

Useful fluorescent labels include umbelliferone, fluorescein, fluorescein isothiocyanate, dichlorotriazinylamine fluorescein, rhodamine, a dansyl group, phycoerythrin, phycocyanin, allophycocyanin, o-phthaldehyde, fluorescamine, and Cy5 (Haugland ((1996) Handbook of Fluorescent Probes and Research Chemicals, Sixth Ed., Molecular Probes, Eugene, Oreg.).

The anti-IL-21 antibodies, or antigen-binding fragments thereof, or IL-21/anti-IL-21 antibody complexes of the present invention can also be detectably labeled using fluorescence-emitting metals such as $^{152}$Eu$^+$, or other members of the lanthanide series, by attaching them using such metal chelating groups as diethylenetriaminepentaacetic acid (DTPA) or ethylenediamine-tetraacetic acid (EDTA).

The anti-IL-21 antibody, or antigen-binding fragment thereof, or IL-21/anti-IL-21 antibody complexes of the present invention can also be detectably labeled by coupling them to a phosphorescent or chemiluminescent compound that can then be detected by the phosphorescence or luminescence that arises during the course of a chemical reaction. Examples of useful chemiluminescent compounds include luminol, isoluminol, theromatic acridinium ester, imidazole, acridinium salt, and oxalate ester. Likewise, a bioluminescent compound such as luciferin, luciferase, or aequorin can be used to label an antibody or antigen-binding fragment thereof of the present invention. The presence of a bioluminescent protein is determined by detecting the presence of luminescence.

An antibody, or antigen-binding fragment thereof, of the present invention can also be attached to solid supports, which are particularly useful for immunoassays or purification of a target antigen. Such solid supports include, e.g., without limitation, beads, e.g., microscopic paramagnetic beads, glass, cellulose, poly-acrylamide, nylon, polystyrene, polyvinyl chloride, or polypropylene.

Use of the Antibodies of the Invention in Immunoassays

A particular protein such as IL-21 can be measured by a variety of immunoassay methods including, e.g., without limitation, competitive and non-competitive assay systems using techniques such as, e.g., without limitation, Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays. For a review of immunological and immunoassay procedures in general, see for example Stites and Terr (eds.) (1991) Basic and Clinical Immunology (7th ed.). Moreover, the immunoassays of the present invention can be performed in many configurations as is known in the art (See for example Maggio (ed.) (1980) Enzyme Immunoassay CRC Press, Boca Raton, Fla.; Gosling J P 2000 Immunoassays: A Practical Approach (Practical Approach Series) Oxford Univ Press; Diamandis Christopoulus, 1996 Immunoassay Academic Press, San Diego, Calif.).

Immunoassays for quantitation can be performed by a variety of art-known methods. In brief, immunoassays to measure IL-21 can be either competitive or noncompetitive binding assays. In competitive binding assays, the sample to be analyzed competes with a labeled analyte for specific binding sites on a capture agent bound to a solid surface. Preferably, the capture agent is an antibody of the present invention, such as Ab2-1, which specifically binds to IL-21. The concentration of labeled analyte bound to the capture agent is inversely proportional to the amount of free analyte present in the sample.

In some embodiments, human IL-21 in a body fluid, e.g., serum or plasma, can be quantified using Quanterix's SIMOA™ technology, which can enable protein quantification at fg/ml levels. SIMOA™ technology (named for single molecule array) is based upon the isolation of individual immunocomplexes on paramagnetic beads using standard ELISA reagents. The main difference between Simoa and conventional immunoassays lies in the ability to trap single molecules in femtoliter-sized wells, allowing for a "digital" readout of each individual bead to determine if it is bound to the target analyte or not. The digital nature of the technique allows an average of 1000×sensitivity increase over conventional assays with CVs<:10%. Commercially available SIMOA™ technology platforms offer multiplexing options up to a 10-plex on a variety of analyte panels, and assays can be automated. Multiplexing experiments can generate large amounts of data. Therefore, in some embodiments, a computer system is utilized to automate and control data collection settings, organization, and interpretation.

In a further embodiment, samples from human normal control and from patients with different diseases (in autoimmune diseases such as psoriasis, systemic lupus erythematosus (SLE), chronic inflammatory bowel disease and Sjogren's Syndrome) in the IL-21 Quanterix SIMOA™ assay can be analysed. An "elevated level" of IL-21 may be determined by comparing the diseased samples to the healthy control samples. The term "elevated level" refers to a "cut point" above which patients may preferentially respond to therapy by administration of a therapeutic antibody that binds to IL-21. Preferably, the "cut point" is 2 standard deviations (SD) above the mean of the healthy controls and is, more preferably. 3 standard deviations (SD) above the mean of the healthy controls.

Any observed significant increases in plasma IL-21 in autoimmune diseases compared with healthy control subjects can be used in patient tailoring whereby a "cut-point" based on IL-21 measurements in a clinical trial is determined. In this regard, IL-21 levels can be used to identify subgroups of patients that preferentially respond to a therapy. This identification can be done with IL-21 levels alone or in combination with other baseline patient characteristics or biomarkers, for example, CRP.

A variety of approaches may be employed to identify IL-21 cut points that define a responding patient subgroup in each disease state or indication of interest Lipkovich I, Dmitrienko A. D'Agostino B R. Tutorial in biostatistics: data-driven subgroup identification and analysis in clinical trials. *Statistics in medicine.* 2017; 36(1): doi:10.1002/sim.7064; Foster J C, Taylor J M G, Ruberg S J. Subgroup identification from randomized clinical trial data. *Statistics in medicine.* 2011; 30(24):10,1002/sim.4322. doi:10.1002/sim.4322; Ruberg S J, Chen L, Wang Y. The mean does not mean as much anymore: finding sub-groups for tailored therapeutics. *Clinical Trials.* 2010; 7(5): doi:10.1177/1740774510369350.

Accordingly, the present invention provides a method of selecting a patient population having an autoimmune disease such as psoriasis, systemic lupus erythematosus (SLE), Crohn's disease, chronic inflammatory bowel disease and Sjogren's Syndrome and having elevated IL-21 levels comprising assaying a plasma sample from a patient, determining levels of IL-21 present and administering an effective amount of a therapeutic IL-21 antibody when the plasma IL-21 levels are elevated.

Another embodiment of the present invention provides a therapeutic antibody that binds to human IL-21 for use in treating an autoimmune disease such as psoriasis, systemic lupus erythematosus (SLE), Crohn's disease, chronic inflammatory bowel disease and Sjogren's Syndrome) in a patient.

An example of a therapeutic IL-21 antibody is one such those disclosed in WO 2015/142637 (Eli Lilly & Company). Such an antibody consists of two antibody heavy chains and two antibody light chains, in which each heavy chain comprises a heavy chain variable domain, the amino acid sequence of which is the sequence of SEQ NO:1 disclosed in WO 2015/142637, and in which each light chain comprises a light chain variable domain, the amino acid sequence of which is the sequence of SEQ ID No: 2. disclosed in WO 2015/142637.

The following examples are offered for illustrative purpose only, and are not intended to limit the scope of the present invention.

EXAMPLE 1

Antibody Expression and Purification

The polypeptides of the variable regions of the heavy chain and light chain, the complete heavy chain and light chain amino acid sequences of anti-human IL-21 antibodies, AbM2, Ab2-1 and Ab3-1, and the nucleotide sequences encoding the same, are listed below in the section entitled "SEQUENCE LISTING". The amino acid sequences and the corresponding SEQ ID NOs of the CDRs of AbM2, Ab2-1 and Ab3-1 are shown below in Tables 1A and 1B the SEQ NOs of the amino acid sequences as well as the encoding DNA sequences of variable regions and full-length of light and heavy chains of AbM2, Ab2-1 and Ab3-1 in Table 1C.

TABLE 1A

|  | LCDR1 | LCDR2 | LCDR3 |
| --- | --- | --- | --- |
| AbM2 | RASQDISNYLN<br>SEQ ID NO: 1 | YTSRLHS<br>SEQ ID NO: 2 | QQFHTLRTF<br>SEQ ID NO: 3 |
| Ab2-1 | RASKSIEKYIA<br>SEQ ID NO: 7 | AGGTLQS<br>SEQ ID NO: 8 | QQHEEYPLT<br>SEQ ID NO: 9 |
| Ab34 | KSSQSLLDVDGKTYLN<br>SEQ ID NO: 13 | LVSKLDS<br>SEQ ID NO: 14 | WQGTHFPYT<br>SEQ ID NO: 15 |

TABLE 1B

|  | HCDR1 | HCDR2 | HCDR3 |
| --- | --- | --- | --- |
| AbM2 | GYTFTDYWMH<br>SEQ ID NO: 4 | LIDTSDSYTIYNQKFKG<br>SEQ ID NO: 5 | YGPLAMDY<br>SEQ ID NO: 6 |
| Ab2-1 | GYDFTGYTMN<br>SEQ ID NO: 10 | LINPYNGGTAYSPKFKG<br>SEQ ID NO: 11 | THYYGSEYTGMDY<br>SEQ ID NO: 12 |
| Ab34 | GYFFTLYMMH<br>SEQ ID NO: 16 | YINPSSGYTEYNQKFKD<br>SEQ ID NO: 17 | DFDY<br>SEQ ID NO: 18 |

TABLE 1C

|       | LCVR |     | HCVR |     | LC  |     | HC  |     |
|-------|------|-----|------|-----|-----|-----|-----|-----|
|       | AA   | DNA | AA   | DNA | AA  | DNA | AA  | DNA |
| AbM2  | 19   | 31  | 20   | 32  | 25  | 33  | 26  | 34  |
| Ab2-1 | 21   | 35  | 22   | 36  | 27  | 37  | 28  | 38  |
| Ab3-1 | 23   | 39  | 24   | 40  | 29  | 41  | 30  | 42  |

The anti-human IL-21 antibodies of the present invention, including, but not limited to, AbM2, Ab2-1 and Ab3, may be expressed transiently in HEK293 or CHO cells using vectors known in the art to be suitable for expression in HEK293 or CHO cells, following standard transfection procedures. Briefly, a recombinant vector or vectors comprising SEQ ID NO: 33 and SEQ ID NO: 34, or SEQ ID NO: 37 and SEQ ID NO: 38, or SEQ ID NO: 41 and SEQ ID NO: 42 may be constructed and used to transiently transfect HEK293 EBNA cells. Transfected cells are cultured in standard serum-free medium 10 containing geneticin (G418) and tobramycin for 48 to 120 hours at 37° C. after transfection. The anti-human IL-21 antibody may be purified using Protein A MabSelect chromatrography resin (GE Healthcare, #17-5199-01) that is pre-equilibrated with PBS, pH7.2, or a HiLoad Superdex 200 26/60 preparative grade size-exclusion chromatography column (GE Healthcare, #28-9893-36) that is pre-equilibrated with PBS, pH7.2. The bound protein is subsequently eluted with 10 mM citrate, pH3 and the pooled fractions immediately neutralized with a 1:10 dilution of 1M Tris, pH8. The neutralized pool is concentrated using Amicon Ultra-15 concentrators (Millipore, #UFC903024).

EXAMPLE 2

IL-21 Antibody Pairing Analysis

Antibodies that may pair (or bind simultaneously) in an ELISA-based assay are determined using a surface plasmon resonance (SPR) assay on a Biacore 2000 instrument primed with HBS-P (GE Healthcare catalog BR-1003-68, 10 mM HEPES pH 7.4+150 mM NaCl+0.0005% surfactant P20) running buffer and analysis temperature at 25° C. A CM4 chip containing immobilized goat anti-mouse IgG Fc specific antibody (Jackson ImmunoResearch catalog 115-005-008) is used to capture an antibody to IL-21. An IL-21 antibody is captured on a test flow cell. Excess Mouse IgG isotype control antibody is injected to block remaining capacity to capture antibody. Human IL-21 is captured by the IL-21 antibody. A second antibody is injected to test for additive binding to the captured IL-21.

The antibodies of the present invention, AbM2, Ab2-1, and Ab3-1, are conjugated to beads (Quanterix Cat #101360) at 0.5 mg/mL and are biotinylated according to the manufacturer's protocol at a ratio of 40 to 1 biotin to antibody. Nine combinations of the three antibody pairs are generated and analyzed against a recombinant IL-21 reference curve (100 ng/mL-1.0 fg/mL). The beads are diluted in bead diluent (Quanterix, Cat #100458) and the detection antibodies are diluted in sample/detection buffer (Quanterix, Cat #101359). Two pairs of antibodies are moved into further optimization due to the ability to discriminate IL-21 concentrations in the fg/mL range. The first pair is Ab2-1 and AbM2 which perform well in either orientation. The second pair is Ab3-21 as capture and Ab2-1 as detection.

Further optimization of the antibody pairs is performed to increase both sensitivity and percent recovery. The concentrations of both the capture and detection antibody are varied in a series of experiments to determine the optimal sensitivity. The capture antibodies are tested at three antibody concentrations (0.1, 0.5, and 1.0 mg/ml). The detection antibodies are tested at three concentrations (0.5, 1.0, and 1.5 mg/ml) using a 40×biotin to antibody ratio. The combinations yield 18 different pairs of antibody combinations. Recombinant human IL-21 protein is used as the standard over a range of 10,000 to 0.64 fg/ml. Antigen is diluted in assay diluent (PBS+1% BSA) (Gibco Cat #20012-043 and Meso Scale Discovery Cat #R93BA-1 respectively). The capture antibodies are diluted in bead diluent (Quanterix, Cat #100458) and the detection antibodies are diluted in the sample/detection buffer (Quanterix, Cat #101359). The optimal pair of antibodies and antibody concentrations is determined to be Ab 2-1 as capture antibody on the bead (1.0 mg/ml) and AbM2 biotinylated as detection (0.5 mg/ml).

Recombinant human IL-21 protein (25-155), as shown in SEQ ID NO: 44, can be expressed in *Escherichia coil* and found as an insoluble inclusion body. The inclusion body is isolated, solubilized in high-concentration urea buffer, and the solubilized material is purified by ion-exchange chromatography. The resulting main peak fractions are pooled and subjected to a sequential dialysis refolding process. The main peak fractions are then purified to homogeneity using reverse-phase chromatography. The main peak fractions are pooled, lyophilized by freeze-drying, resuspended in PBS, pH7.2 buffer and stored at −80 C as working aliquots.

EXAMPLE 3

Quanterix Simoa™ Assay

Anti-IL-21 antibody Ab2-1 is conjugated to carboxylated paramagnetic beads (Quanterix Cat #100451) according to the standard Quanterix protocol at 1.0 mg/ml. Anti-IL-21 antibody AbM2 is biotinylated according to the standard Quanterix protocol (40:1 biotin ratio). For each run on the Quanterix, Ab2-1 beads (approximately 5 million beads/ml) are prepared in bead diluent (Quanterix Cat #100458) and biotinylated AbM2 antibody (0.5 µg/mL) is diluted in sample/detection buffer (Quanterix Cat #101359) to appropriate volumes. Streptavidin-beta-galactosidase (SBG) (Quanterix Cat #100439) is prepared in SBG diluent (Quanterix Cat #100376) at 150 pM. IL-21 recombinant protein or samples are diluted in assay buffer (600 mM NaCl, 0.5% Tween 20, 25% FBS, 2% BSA and 200 HBR in PBS (Boston BioProducts Cat #BM-244; Thermo Scientific Cat #28320; Gibco Cat #16010-159; Meso Scale Discovery Cat #R93BA-2; Scantibodies Cat #3KC534-075 and Hyclone Cat #SH30258.01 respectively) at appropriate dilutions. Ab2-1 beads, biotinylated AbM2 antibody, calibrators, SBG, and supplied resorufin-beta-D galactopyranoside (RGP) (Quanterix Cat #10030) reagents are loaded into the instrument and run as a two-step Homebrew method according to the Simoa™ HD-1 Analyzer User Guide at room temperature. Binding data of Ab2-1 to recombinant human IL-21 protein is shown in Table 1 and Figure 1. To determine the spike and recovery in the Quanterix Simoa assay, different amounts of recombinant IL-21 are spiked into the human serum matrix. The percentage recovery is summarized in Table 2 and Figures 2 and 3. LLOQ in serum matrix was calculated as 30 fg/ml. Exploratory Validation has also been done in heparin plasma with comparable results for dilutional linearity, spike recovery and total error.

TABLE 1

IL-21 Quanterix Assay Binding Data

| IL-21 (pg/ml) | Replicate 1 AEB* | Replicate 2 AEB* |
|---|---|---|
| 5 | 4.049 | 4.080 |
| 1.25 | 1.145 | 1.318 |
| 0.3125 | 0.324 | 0.324 |
| 0.078125 | 0.098 | 0.101 |
| 0.01953125 | 0.026 | 0.030 |
| 0.004882813 | 0.010 | 0.013 |
| 0.001220703 | 0.008 | 0.009 |
| 0.000305176 | 0.006 | 0.006 |

*AEB = average enzyme per bead

The data in Table 1 and Figure 1 demonstrate that the IL-21 Quanterix assay has a large dynamic range from 0.0003-5 pg/ml of IL-21 with a lower limit of Quantification of 0.03 pg/ml as calculated in serum matrix.

TABLE 2

IL-21 spike and recovery in human serum

| Pg/ml | % Recovery |
|---|---|
| 2.5 | 86 |
| 0.625 | 87 |
| 0.156 | 95 |
| 0.039 | 93 |
| 0.010 | 100 |
| 0.002 | 103 |
| 0.001 | 95 |

The developed IL-21 Quanterix Simoa assay demonstrates an acceptable percent recovery for a given amount of IL-21 in serum.

EXAMPLE 4

Analysis of Human Normal Control Samples and Diseased Samples in the IL-21 Quanterix SIMOA™ Assay Human normal control samples and Sjögren's and SLE patient samples, including 13 healthy, 11 Sjögren's, and 14 SLE serum samples, are run in the IL-21 Quanterix SIMOA™ Homebrew assay. The samples are run in a Quanterix SIMOA™ Homebrew assay at a 1:2 dilution in the IL-21 Assay Buffer: NaCl (600 mM, Boston BioProducts, Cat #BM-244), newborn calf serum (25%, Gibco, Cat #16010-159), tween 20 (0.5%, Thermo Scientific, Cat #28320), BSA (2%, MSD, Cat #R93BA-2), and Heterophilic blocker (20 ug/ml, Scantibodies, Cat #3KC534-075) in PBS (1×, Hyclone, cat #SH30258.01) Ab 2.1 antibody is conjugated to beads for capture, and biotinylated AbM2 for detection. The results are presented in Figure 1. There is a significant difference in IL-21 levels between the normal healthy controls and both the Sjögren's and SLE patients' serum. In this regard, significant increases in plasma IL-21 in autoimmune diseases vs. healthy control subjects were observed.

```
                        SEQUENCE LISTING

SEQ ID NO: 1; PRT1; Artificial sequence
RASQDISNYLN

SEQ ID NO: 2; PRT1; Artificial sequence
YTSRLHS

SEQ ID NO: 3; PRT1; Artificial sequence
QQFHTLRTF

SEQ ID NO: 4; PRT1; Artificial sequence
GYTFTDYWMH

SEQ ID NO: 5; PRT1; Artificial sequence
LIDTSDSYTIYNQKFKG

SEQ ID NO: 6; PRT1; Artificial sequence
YGPLAMDY

SEQ ID NO: 7; PRT1; Artificial sequence
RASKSIEKYIA

SEQ ID NO: 8; PRT1; Artificial sequence
AGGTLQS

SEQ ID NO: 9; PRT1; Artificial sequence
QQHEEYPLT

SEQ ID NO: 10: PRT1; Artificial sequence
GYDFTGYTMN

SEQ ID NO: 11; PRT1; Artificial sequence
LINPYNGGTAYSPKFKG

SEQ ID NO: 12; PRT1; Artificial sequence
THYYGSEYTGMDY

SEQ ID NO: 13; PRT1; Artificial sequence
KSSQSLLDVDGKTYLN
```

SEQUENCE LISTING

SEQ ID NO: 14; PRT1; Artificial sequence
LVSKLDS

SEQ ID NO: 15; PRT1; Artificial sequence
WQGTHFPYT

SEQ ID NO: 16; PRT1; Artificial sequence
GYFFTLYMMH

SEQ ID NO: 17; PRT1; Artificial sequence
YINPSSGYTEYNQKFKD

SEQ ID NO: 18; PRT1; Artificial sequence
DFDY

SEQ ID NO: 19; PRT1; Artificial sequence
DIQMTQSPSSLSASVGDRVTITCRASQDISNYLNWYQQKPGKAPKLLIYYTSRLHS
GVPSRFSGSGSGTDFTLTISSLQPEDFATYYCQQFHTLRTFGGGTKVEIK SEQ ID NO: 20; PRT1; Artificial sequence
QVQLVQSGAEVKKPGASVKVSCKASGYTFTDYWMHWVRQAPGQGLEWMGLID
TSDSYTIYNQKFKGRVTMTRDTSTSTVYMELSSLRSEDTAVYYCARYGPLAMDY
WGQGTLVTVSS SEQ ID NO: 21; PRT1; Artificial sequence
DIQMNQSPSYLAASPGETITINCRASKSIEKYIAWYQEKPGKTNKLLIYAGGTLQS
GIPSRFSGSGSGTDFTLTISSLEPEDFAMYYCQQHEEYPLTFGAGTKLELK SEQ ID NO: 22; PRT1; Artificial sequence
QVQLQQSGPELVKPGASMKISCKASGYDFTGYTMNWVKQSHGKNLEWIGLINP
YNGGTAYSPKFKGKATLTVDKSSSTVYMELLSLTSEDSAVYHCARTHYYGSEYT
GMDYWGQGTSVTVSS SEQ ID NO: 23; PRT1; Artificial sequence
DIQVTQTPLTLSVTIGQPASISCKSSQSLLDVDGKTYLNWLLQRPGQSPKRLIYLVS
KLDSGVPDRFTGSGSGTDFTLRISRVEAEDLGVYYCWQGTHFPYTFGGGTRLEIK SEQ ID NO: 24; PRT1; Artificial sequence
QVQLKQSAAELARPGASVKMSCKASGYFFTLYMMHWAKQRPGQNLEWIGYINP
SSGYTEYNQKFKDKTTLTADKSSSTAYMQLSSLTSEDSAIYYCLTDFDYWGQGTS
LTVSS SEQ ID NO: 25; PRT1; Artificial sequence
DIQMTQSPSSLSASVGDRVTITCRASQDISNYLNWYQQKPGKAPKLLIYYTSRLHS
GVPSRFSGSGSGTDFTLTISSLQPEDFATYYCQQFHTLRTFGGGTKVEIKRTVAAP
SVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC SEQ ID NO: 26; PRT1; Artificial sequence
QVQLVQSGAEVKKPGASVKVSCKASGYTFTDYWMHWVRQAPGQGLEWMGLID
TSDSYTIYNQKFKGRVTMTRDTSTSTVYMELSSLRSEDTAVYYCARYGPLAMDY
WGQGTLVTVSSASTKGPSVFPLAPCSRSTSESTAALGCLVKDYFPEPVTVSWNSG
ALTSGVHTFPAVLQSSGLYSLSSVVTVPSSSLGTKTYTCNVDHKPSNTKVDKRVE
SKYGPPCPPCPAPEAAGGPSVFLFPPKPKDTLMISRTPEVTCVVVDVSQEDPEVQF
NWYVDGVEVHNAKTKPREEQFNSTYRVVSVLTVLHQDWLNGKEYKCKVSNKG
LPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYT
QKSLSLSLG SEQ ID NO: 27; PRT1; Artificial sequence
DIQMNQSPSYLAASPGETITINCRASKSIEKYAWYQEKPGKTNKLLIYAGGTLQS
GIPSRFSGSGSGTDFTLTISSLEPEDFAMYYCQQHEEYPLTFGAGTKLELKRADAA
PTVSIFPPSSEQLTSGGASVVCFLNNFYPKDINVKWKIDGSERQNGVLNSWTDQD
SKDSTYSMSSTLTLTKDEYERHNSYTCEATHKTSTSPIVKSFNRNEC SEQ ID NO: 28; PRT1; Artificial sequence
QVQLQQSGPELVKPGASMKISCKASGYDFTGYTMNWVKQSHGKNLEWIGLINP
YNGGTAYSPKFKGKATLTVDKSSSTVYMELLSLTSEDSAVYHCARTHYYGSEYT
GMDYWGQGTSVTVSSAKTTPPSVYPLAPGSAAQTNSMVTLGCLVKGYFPEPVTV
TWNSGSLSSGVHTFPAVLQSDLYTLSSSVTPSSTWPSETVTICNVAHPASSTKVD
KKIVPRDCGCKPCICTVPEVSSVFIFPPKPKDVLTITLTPKVTCVVVDISKDDPEVQ
FSWFVDDVEVHTAQTQPREEQFNSTFRSVSELPIMHQDWLNGKEFKCRVNSAAF
PAPIEKTISKTKGRPKAPQVYTIPPPKEQMAKDKVSLTCMITDFFPEDITVEWQWN
GQPAENYKNTQPIMDTDGSYFVYSKLNVQKSNWEAGNTFTCSVLHEGLHNHHT
EKSLSHSPGK

SEQUENCE LISTING

SEQ ID NO: 29; PRT1; Artificial sequence
DIQVTQTPLTISVTIGQPASISCKSSQSLLDVDGKTYLNWLLQRPGQSPKRLIYLVS
KLDSGVPDRFTGSGSGTDFTLRISRVEAEDLGVYYCWQGTHFPYTFGGGTRLEIK
RADAAPTVSIFPPSSEQLTSGGASVVCFLNNFYPKDINVKWKIDGSERQNGVLNS
WTDQDSKDSTYSMSSTLTLTKDEYERHNSYTCEATHKTSTSPIVKSFNRNEC SEQ ID NO: 30; PRT1; Artificial sequence
QVQLKQSAAELARPGASVKMSCKASGYFFTLYMMHWAKQRPGQNLEWIGYINP
SSGYTEYNQKFKDKTTLTADKSSSTAYMQLSSLTSEDSAIYYCLTDFDYWGQGTS
LTVSSAKTTPPSVYPLAPGSAAQTNSMVTLGCLVKGYFPEPVTVTWNSGSLSSGV
HTFPAVLQSDLYTLSSSVTYPSSTWPSETVTCNVAHPASSTKVDKKIVPRDCGCK
PCICTVPEVSSVFIFPPKPKDVLTITLTPKVTCVVVDISKDDPEVQFSWFVDDVEVH
TAQTQPREEQPNSTFRSVSELPIMHQDWLNGKEFKCRVNSAAFPAPIEKTISKTKG
RPKAPQVYTIPPPKEQMAKDKVSLTCMITDFFPEDITVEWQWNGQPAENYKNTQ
PIMDTDGSYFVYSKLNVQKSNWEAGNTFTCSVLHEGLHNHHTEKSLSHSPGK SEQ ID NO: 31 DNA; Artificial Sequence
GACATCCAGATGACCCAGTCTCCATCCTCCCTGTCTGCATCTGTAGGAGACAG
AGTCACCATCACTTGCAGGGCAAGTCAGGACATTAGCAATTATTTAAACTGGT
ATCAGCAGAAACCAGGGAAAGCCCCTAAGCTCCTGATCTATTACACATCAAG
ATTACACTCAGGGGTCCCATCAAGGTTCAGTGGCAGTGGATCTGGGACAGAT
TTCACTCTCACCATCAGCAGTCTGCAACCTGAAGATTTTGCAACTTACTACTG
TCAACAGTTTCACACGCTTCGGACGTTCGGCGGAGGGACCAAGGTGGAGATC
AAA SEQ ID NO: 32; DNA; Artificial Sequence
CAGGTGCAGCTGGTGCAGTCTGGGGCTGAGGTGAAGAAGCCTGGGGCCTCAG
TGAAGGTTTCCTGCAAGGCATCTGGCTACACATTCACTGACTACTGGATGCAC
TGGGTGCGACAGGCCCCTGGACAAGGGCTTGAGTGGATGGGACTGATTGATA
CTTCTGATAGTTATACTATCTACAATCAAAAGTTCAAGGGCAGAGTCACCATG
ACCAGGGACACGTCCACGAGCACAGTCTACATGGAGCTGAGCAGCCTGAGAT
CTGAGGACACGGCCGTGTATTACTGTGCAAGATATGGGCCCCTGGCTATGGA
CTACTGGGGCCAGGGCACCCTGGTCACCGTCTCCTCA SEQ ID NO: 33; DNA; Artificial Sequence
GACATCCAGATGACCCAGTCTCCATCCTCCCTGTCTGCATCTGTAGGAGACAG
AGTCACCATCACTTGCAGGGCAAGTCAGGACATTAGCAATTATTTAAACTGGT
ATCAGCAGAAACCAGGGAAAGCCCCTAAGCTCCTGATCTATTACACATCAAG
ATTACACTCAGGGGTCCCATCAAGGTTCAGTGGCAGTGGATCTGGGACAGAT
TTCACTCTCACCATCAGCAGTCTGCAACCTGAAGATTTTGCAACTTACTACTG
TCAACAGTTTCACACGCTTCGGACGTTCGGCGGAGGGACCAAGGTGGAGATC
AAAAGAACTGTGGCGGCGCCATCTGTCTTCATCTTCCCGCCATCTGATGAGCA
GTTGAAATCCGGAACTGCCTCTGTTGTGTGCCTGCTGAATAACTTCTATCCCA
GAGAGGCCAAAGTACAGTGGAAGGTGGATAACGCCCTCCAATCGGGTAACTC
CCAGGAGAGTGTCACAGAGCAGGACAGCAAGGACAGCACCTACAGCCTCAG
CAGCACCCTGACGCTGAGCAAAGCAGACTACGAGAAACACAAAGTCTACGCC
TGCGAAGTCACCCATCAGGGCCTGAGCTCGrCCCGTCACAAAGAGCTTCAACA
GGGGAGAGTGC SEQ ID NO: 34; DNA; Artificial Sequence
CAGGTGCAGCTGGTGCAGTCTGGGGCTGAGGTGAAGAAGCCTGGGGCCTCAG
TGAAGGTTTCCTGCAAGGCATCTGGCTACACATTCACTGACTGGATGCAC
TGGGTGCGACAGGCCCCTGGACAAGGGCTTGAGTGGATGGGACTGATTGATA
CTTCTGATAGTTATACTATCTACAATCAAAAGTTCAAGGGCAGAGTCACCATG
ACCAGGGACACGTCCACGAGCACAGTCTACATGGAGCTGAGCAGCCTGAGAT
CTGAGGACACGGCCGTGTATTACTGTGCAAGATATGGGCCCCTGGCTATGGA
CTACTGGGGCCAGGGCACCCTGGTCACCGTCTCCTCAGCCTCCACCAAGGGCC
CATCGGTCTTCCCGCTAGCGCCCTGCTCCAGGAGCACCTCCGAGAGCACAGCC
GCCCTGGGCTGCCTGGTCAAGGACTACTTCCCCGAACCGGTGACGGTGTCGTG
GAACTCAGGCGCCCTGACCAGCGGCGTGCACACCTTCCCGGCTGTCCTACAGT
CCTCAGGACTCTACTCCCTCAGCAGCGTGGTGACCGTGCCCTCCAGCAGCTTG
GGCACGAAGACCTACACCTGCAACGTAGATCACAAGCCCAGCAACACCAAGG
TGGACAAGAGAGTTGAGTCCAAATATGGTCCCCCATGCCCACCCTGCCCAGC
ACCTGAGGCCGCCGGGGGACCATCAGTCTTCCTGTTCCCCCCAAAACCCAAG
GACACTCTCATGATCTCCCGGACCCCTGAGGTCACGTGCGTGGTGGTGGACGT
GAGCCAGGAAGACCCCGAGGTCCAGTTCAACTGGTACGTGGATGGCGTGGAG
GTGCATAATGCCAAGACAAAGCCGCGGGAGGAGCAGTTCAACAGCACGTACC
GTGTGGTCAGCGTCCTCACCGTCCTGCACCAGGACTGGCTGAACGGCAAGGA
GTACAAGTGCAAGGTCTCCAACAAAGGCCTCCCGTCCTCCATCGAGAAAACC
ATCTCCAAAGCCAAAGGGCAGCCCCGAGAGCCACAGGTGTACACCCTGCCCC
CATCCCAGGAGGAGATGACCAAGAACCAGGTCAGCCTGACCTGCCTGGTCAA
AGGCTTCTACCCCAGCGACATCGCCGTGGAGTGGGAAAGCAATGGGCAGCCG
GAGAACAACTACAAGACCACGCCTCCCGTGCTGGACTCCGACGGCTCCTTCTT
CCTCTACAGCAGGCTAACCGTGGACAAGAGCAGGTGGCAGGAGGGGAATGTC
TTCTCATGCTCCGTGATGCATGAGGCTCTGCACAACCACTACACACAGAAGA
GCCTCTCCCTGTCTCTGGGT

SEQUENCE LISTING

SEQ ID NO: 35; DNA; Artificial Sequence
GACATCCAGATGAACCAGTCTCCATCTTATCTTGCTGCATCTCCTGGAGAAAC
CATTACTATTAATTGCAGGGCAAGTAAGAGCATTGAGAAATATATCGCCTGG
TATCAAGAGAAACCTGGGAAAACTAATAAGCTTCTTATCTACGCAGGAGGCA
CTTTGCAATCTGGAATTCCATCAAGGTTCAGTGGCAGTGGATCTGGTACAGAT
TTCACTCTCACCATCAGTAGCCTGGAGCCTGAAGATTTTGCAATGTATTACTG
TCAACAGCATGAGGAATACCCGCTCACGTTCGGTGCTGGGACCAAGCTGGAG
CTGAAA SEQ ID NO: 36; DNA; Artificial Sequence
CAGGTCCAGCTGCAGCAGTCTGGACCTGAGCTGGTGAAGCCTGGAGCTTCAA
TGAAGATATCCTGCAAGGCTTCTGGTTACGACTTCACTGGCTACACCATGAAC
TGGGTGAAGCAGAGCCATGGAAAGAACCTTGAGTGGATTGGACTTATTAATC
CTTACAATGGTGGTACTGCCTACAGCCCTAAGTTCAAGGGCAAGGCCACATT
AACTGTAGACAAGTCATCCAGCACAGTCTACATGGAGCTCCTCAGTCTGACAT
CTGAGGACTCTGCAGTCTATCACTGTGCAAGGACTCACTACTACGGAAGTGA
ATACACTGGTATGGACTACTGGGGTCAAGGAACCTCAGTCACCGTCTCCTCA SEQ ID NO: 37; DNA; Artificial Sequence
GACATCCAGATGAACCAGTCTCCATCTTATCTTGCTGCATCTCCTGGAGAAAC
CATTACTATTAATTGCAGGGCAAGTAAGAGCATTGAGAAATATATCGCCTGG
TATCAAGAGAAACCTGGGAAAACTAATAAGCTTCTTATCTACGCAGGAGGCA
CTTTGCAATCTGGAATFCCATCAAGGTTCAGTGGCAGTGGATCTGGTACAGAT
TTCACTCTCACCATCAGTAGCCTGGAGCCTGAAGATTTTGCAATGTATTACTG
TCAACAGCATGAGGAATACCCGCTCACGTTCGGTGCTGGGACCAAGCTGGAG
CTGAAACGGGCTGATGCGGCGCCCACTGTATCCATCTTCCCACCATCCAGTGA
GCAGTTAACATCTGGAGGTGCTAGCGTCGTGTGCTTCTTGAACAACTTCTACC
CCAAAGACATCAATGTCAAGTGGAAGATTGATGGCAGTGAACGACAAAATGG
CGTCCTGAACAGTTGGACTGATCAGGACAGCAAAGACAGCACCTACAGCATG
AGCAGCACCCTCACGTTGACCAAGGACGAGTATGAACGACATAACAGCTATA
CCTGTGAGGCCACTCACAAGACATCAACTTCACCCATTGTCAAGAGCTTCAAC
AGGAATGAGTGT SEQ ID NO: 38; DNA; Artificial Sequence
CAGGTCCAGCTGCAGCAGTCTGGACCTGAGCTGGTGAAGCCTGGAGCTTCAA
TGAAGATATCCTGCAAGGCTTCTGGTTACGACTTCACTGGCTACACCATGAAC
TGGGTGAAGCAGAGCCATGGAAAGAACCTTGAGTGGATTGGACTTATTAATC
CTTACAATGGTGGTACTGCCTACAGCCCTAAGTTCAAGGGCAAGGCCACATT
AACTGTAGACAAGTCATCCAGCACAGTCTACATGGAGCTCCTCAGTCTGACAT
CTGAGGACTCTGCAGTCTATCACTGTGCAAGGACTCACTACTACGGAAGTGA
ATACACTGGTATGGACTACTGGGGTCAAGGAACCTCAGTTACCGTCTCCTCAG
CCAAAACGACACCCCCATCTGTCTATCCGCTAGCCCCTGGATCTGCCGCCCAG
ACCAACAGCATGGTGACCCTGGGCTGTCTGGTGAAGGGCTACTTCCCTGAGC
CTGTGACAGTGACCTGGAACAGCGGCTCTCTGTCTAGCGGCGTGCACACATTC
CCTGCCGTGCTGCAGAGCGACCTGTACACCCTGAGCAGCAGCGTGACCGTGC
CTAGCAGCACATGGCCTAGCGAGACCGTGACATGCAACGTGGCCCACCCTGC
CTCTTCTACCAAGGTGGACAAGAAGATCGTGCCCAGAGACTGCGGCTGCAAG
CCTTGCATCTGCACCGTGCCTGAGGTGAGCAGCGTGTTCATCTTCCCACCCAA
GCCCAAGGACGTGCTCACCATCACCCTCACCCCCAAGGTCACGTGTGTTGTGG
TAGACATCAGCAAGGATGATCCCGAGGTCCAGTTCAGCTGGTTTGTAGATGA
TGTGGAGGTGCACACAGCTCAGACGCAACCCCGGGAGGAGCAGTTCAACAGC
ACTTTCCGCTCAGTCAGTGAACTTCCCATCATGCACCAGGACTGGCTCAATGG
CAAGGAGTTCAAATGCAGGGTCAACAGTGCAGCTTTCCCTGCCCCCATCGAG
AAAACCATCTCCAAAACCAAAGGCAGACCGAAGGCTCCACAGGTGTACACCA
TTCCACCTCCCAAGGAGCAGATGGCCAAGGATAAAGTCAGTCTGACCTGCAT
GATAACAGACTTCTTCCCTGAAGACATTACTGTGGAGTGGCAGTGGAATGGG
CAGCCAGCGGAGAACTACAAGAACACTCAGCCCATCATGGACACAGATGGCT
CTTACTTCGTCTACAGCAAGCTCAATGTGCAGAAGAGCAACTGGGAGGCAGG
AAATACTTTCACCTGCTCTGTGTTACATGAGGGCCTGCACAACCACCATACTG
AGAAGAGCCTCTCCCACTCTCCTGGTAAA SEQ ID NO: 39; DNA; Artificial Sequence
GACATCCAGGTGACTCAGACTCCACTCACTTTGTCGGTTACCATTGGACAACC
AGCCTCCATCTCTTGCAAGTCAAGTCAGAGCCTCTTAGATGTGGATGGAAAG
ACATATTTGAATTGGTTGTTACAGAGGCCAGGCCAGTCTCCAAAGCGCCTAAT
CTATCTGGTGTCTAAACTGGACTCTGGAGTCCCTGACAGGTTCACTGGCAGTG
GATCAGGGACAGATTTCACACTGAGAATCAGCAGAGTGGAGGCTGAGGATTT
GGGAGTTTATTATTGCTGGCAAGGTACACATTTTCCTTACACGTTCGGAGGGG
GGACCAGACTGGAAATAAAA SEQ ID NO: 40; DNA; Artificial Sequence
CAGGTGCAGCTGAAGCAGTCTGCAGCTGAACTGGCAAGACCTGGGGCCTCAG
TGAAGATGTCCTGCAAGGCTTCTGGCTATTTTTTACCCTGTACATGATGCACT
GGGCAAAACAGAGGCCTGGACAGAATCTGGAATGGATTGGATACATTAATCC
TAGCAGTGGATATACTGAATACAATCAGAAGTTCAAGGACAAGACCACATTG
ACTGCAGACAAATCCTCCAGCACAGCCTACATGCAACTGAGCAGCCTGACAT

CTGAGGATTCTGCGATCTATTACTGTCTAACGGACTTTGACTACTGGGGCCAA
GGCACCAGTCTCACAGTCTCCTCA

SEQ ID NO: 41; DNA; Artificial Sequence
GACATCCAGGTGACTCAGACTCCACTCACTTTGTCGGTTACCATTGGACAACC
AGCCTCCATCTCTTTCAAGTCAAGTCAGAGCCTCTTAGATGTGGATGGAAAG
ACATATTTGAATTGGTTGTTACAGAGGCCAGGCCAGTCTCCAAAGCGCCTAAT
CTATCTGGTGTCTAAACTGGACTGTGGAGTCCCTGACAGGTTCACTGGCAGTG
GATCAGGGACAGATTTCACACTGAGAATCAGCAGAGTGGAGGCTGAGGATTT
GGGAGTTTATTATTGCTGGCAAGGTACACATTTTCCTTACACGTTCGGAGGGG
GGACCAGACTGGAAATAAAACGGGCTGATGCTGCGCCCACTGTATCCATCTT
CCCACCATCCAGTGAGCAGTTAACATCTGGAGGTGCTAGCGTCGTGTGCTTCT
TGAACAACTTCTACCCCAAAGACATCAATGTCAAGTGGAAGATTGATGGCAG
TGAACGACAAAATGGCGTCCTGAACAGTTGGACTGATCAGGACAGCAAAGAC
AGCACCTACAGCATGAGCAGCACCCTCACGTTGACCAAGGACGAGTATGAAC
GACATAACAGCTATACCTGTGAGGCCACTCACAAGACATCAACTTCACCCATT
GTCAAGAGCTTCAACAGGAATGAGTGT SEQ ID NO: 42; DNA; Artificial Sequence
CAGGTGCAGCTGAAGCAGTCTGCAGCTGAACTGGCAAGACCTGGGGCCTCAG
TGAAGATGTCCTGCAAGGCTTCTGGCTATTTTTTACCCTGTACATGATGCACT
GGGCAAAACAGAGGCCTGGACAGAATCTGGAATGGATTGGATACATTAATCC
TAGCAGTGGATATACTGAATACAATCAGAAGTTCAAGGACAAGACCACATTG
ACTGCAGACAAATCCTCCAGCACAGCCTACATGCAACTGAGCAGCCTGACAT
CTGAGGATTCTGCGATCTATTACTGTCTAACGGACTTTGACTACTGGGGCCAA
GGCACCAGTCTCACAGTTTCCTCAGCCAAAACGACACCCCCATCTGTCTATCC
GCTAGCCCCTGGATCTGCCGCCCAGACCAACAGCATGGTGACCCTGGGCTGT
CTGGTGAAGGGCTACTTCCCTGAGCCTGTGACAGTGACCTGGAACAGCGGCT
CTCTGTCTAGCGGCGTGCACACATTCCCTGCCGTGCTGCAGAGCGACCTGTAC
ACCCTGAGCAGCAGCGTGACCGTGCCTAGCAGCACATGGCCTAGCGAGACCG
TGACATGCAACGTGGCCCACCCTGCCTCTTCTACCAAGGTGGACAAGAAGAT
CGTGCCCAGAGACTGCGGCTGCAAGCCTTGCATCTGCACCGTGCCTGAGGTG
AGCAGCGTGTTCATCTTCCCACCCAAGCCCAAGGACGTGCTCACCATCACCCT
CACCCCCAAGGTCACGTGTGTTGTGGTAGACATCAGCAAGGATGATCCCGAG
GTCCAGTTCAGCTGGTTTGTAGATGATGTGGAGGTGCACACAGCTCAGACGC
AACCCCGGGAGGAGCAGTTCAACAGCACTTTCCGCTCAGTCAGTGAACTTCC
CATCATGCACCAGGACTGGCTCAATGGCAAGGAGTTCAAATGCAGGGTCAAC
AGTGCAGCTTTCCCTGCCCCCATCGAGAAAACCATCTCCAAAACCAAAGGCA
GACCGAAGGCTCCACAGGTGTACACCATTCCACCTCCCAAGGAGCAGATGGC
CAAGGATAAAGTCAGTCTGACCTGCATGATAACAGACTTCTTCCCTGAAGAC
ATTACTGTGGAGTGGCAGTGGAATGGGCAGCCAGCGGAGAACTACAAGAAC
ACTCAGCCCATCATGGACACAGATGGCTCTTACTTCGTCTACAGCAAGCTCAA
TGTGCAGAAGAGCAACTGGGAGGCAGGAAATACTTTCACCTGCTCTGTGTTA
CATGAGGGCCTGCACAACCACCATACTGAGAAGAGCCTCTCCCACTCTCCTG
GTAAA SEQ ID NO:43; PRT1; homo sapiens
MRSSPGNMERIVICLMVIFLGTLVHKSSSQGQDRHMIRMRQLIDIVDQLKNYVND
LVPEFLPAPEDVETNCEWSAFSCFQKAQLKSANTGNNERIINVSIKKLKRKPPSTN
AGRRQKHRLTCPSCDSYEKKPPKEFLERFKSLLQKMIHQHLSSRTHGSEDSS SEQ ID NO: 44; PRT1; Artificial sequence
MQDRHMIRMRQLIDIVDQLKNYVNDLVPEFLPAPEDVETNCEWSAFSCFQKAQL
KSANTGNNERIINVSIKKLKRKPPSTNAGRRQKHRLTCPSCDSYEKKPPKEFLERF
KSLLQKMIHQHLSSRTHGSEDS SEQ ID NO: 45; DNA; homo sapiens
ATGAGATCCAGTCCTGGCAACATGGAGAGGATTGTCATCTGTCTGATGGTCAT
CTTCTTGGGGACACTGGTCCACAAATCAAGCTCCCAAGGTCAAGATCGCCAC
ATGATTAGAATGCGTCAACTTATAGATATTGTTGATCAGCTGAAAAATTATGT
GAATGACTTGGTCCCTGAATTTCTGCCAGCTCCAGAAGATGTAGAGACAAAC
TGTGAGTGGTCAGCTTTTTCCTGCTTTCAGAAGGCCCAACTAAAGTCAGCAAA
TACAGGAAACAATGAAAGGATAATCAATGTATCAATTAAAAAGCTGAAGAG
GAAACCACCTTCCACAAATGCAGGGAGAAGACAGAAACACAGACTAACATG
CCCTTCATGTGATTCTTATGAGAAAAAACCACCCAAAGAATTCCTAGAAAGA
TTCAAATCACTTCTCCAAAAGATGATTCATCAGCATCTGTCCTCTAGAACACA
CGGAAGTGAAGATTCCTGA

We claim:

1. An in vitro method of detecting human IL-21 in a sample of tissue or body fluid comprising:
   a) contacting said sample with a first antibody or antigen-binding fragment thereof that specifically binds to human-IL-21, wherein a complex of the first antibody or antigen-binding fragment thereof and human-IL-21 is formed, and capturing the complex on a solid support, wherein said first antibody or antigen-binding fragment thereof comprises a light chain variable region (LCVR) and a heavy chain variable region (HCVR), wherein said LCVR comprises three light chain complementarity determining regions (LCDRs) and said HCVR comprises three heavy chain complementarity determining regions (HCDRs), wherein the amino acid sequences of said three LCDRs and said three HCDRs comprise: RASQDISNYLN (SEQ ID NO: 1), YTSRLHS (SEQ ID NO: 2), QQFHTLRTF (SEQ ID NO: 3), GYTFTDYWMH (SEQ ID NO: 4), LIDTSDSYTIYNQKFKG (SEQ ID NO: 5), and YGPLANIDY (SEQ ID NO: 6) respectively;
   b) removing non-specifically bound first antibody or antigen-binding fragment thereof; and
   c) detecting the complex of the first antibody or antigen-binding fragment thereof and human-IL-21 with a second antibody or an antigen-binding fragment thereof that specifically binds human-IL-21, wherein the second antibody or antigen-binding fragment thereof comprises a detectable label, and wherein said second antibody or antigen-binding fragment thereof comprises a light chain variable region (LCVR) and a heavy chain variable region (HCVR), wherein said LCVR comprises three light chain complementarity determining regions (LCDRs) and said HCVR comprises three heavy chain complementarity determining regions (HCDRs), wherein the amino acid sequences of said three LCDRs and said three HCDRs are selected from the group consisting of:

i) RASKSIEKYIA (SEQ ID NO: 7), AGGTLQS (SEQ ID NO: 8), QQHEEYPLT (SEQ ID NO: 9), GYDFTGYTMN (SEQ ID NO: 10), LINPYN-GGTAYSPKFKG (SEQ ID NO: 11), and THYYG-SEYTGMDY (SEQ ID NO: 12) respectively; and
   ii) KSSQSLLDVDGKTYLN (SEQ ID NO: 13), LVSKLDS (SEQ ID NO: 14), WQGTHFPYT (SEQ ID NO: 15), GYFFTLYMNIH (SEQ ID NO: 16), YINPSSGYTEYNQKFKD (SEQ ID NO: 17), and DFDY (SEQ ID NO: 18) respectively.

2. The method of claim 1, wherein the LCVR and HCVR of said first antibody or antigen-binding fragment thereof comprise the amino sequence of SEQ ID NO: 19 and the amino sequence of SEQ ID NO: 20, respectively.

3. The method of claim 1, wherein the light chain and the heavy chain of said first antibody comprise the amino sequence of SEQ ID NO:25 and the amino sequence of SEQ ID NO:26, respectively.

4. The method of claim 1, wherein said LCVR and said HCVR of said second antibody, or antigen-binding fragment thereof, consisting of the amino sequence of SEQ ID NO: 21 and the amino sequence of SEQ ID NO:22 respectively.

5. The method of claim 1, wherein said LCVR and said HCVR of said second antibody, or antigen-binding fragment thereof, consisting of the amino sequence of SEQ ID NO: 23 and the amino sequence of SEQ ID NO:24 respectively.

6. The method of claim 1, wherein the light chain and the heavy chain of said second antibody comprise the amino sequence of SEQ ID NO:27 and the amino sequence of SEQ ID NO:28, respectively.

7. The method of claim 1, wherein the light chain and the heavy chain of said second antibody comprise the amino sequence of SEQ ID NO:29 and the amino sequence of SEQ ID NO:30, respectively.

8. The method of claim 1, wherein the second antibody comprises two light chains and two heavy chains, wherein the amino acid sequences of each of said light chains and each of said heavy chains are selected from the group consisting of:

a) the amino sequence of SEQ ID NO:27 and the amino sequence of SEQ ID NO:28; and
b) the amino sequence of SEQ ID NO:29 and the amino sequence of SEQ ID NO:30.

9. The method of claim 1, wherein said detectable label is selected from the group consisting of a chromophore, a chromogen, a dye, a fluorescent agent, a fluorogenic agent, a phosphorescent agent, a chemiluminescent agent, a bioluminescent agent, a radionuclide, a positron emission tomography-imageable agent, and a magnetic resonance-imageable agent.

10. The method of claim 1, further comprising the step of quantifying the amount of the complex of the first antibody or antigen-binding fragment thereof and human-IL-21.

* * * * *